United States Patent
Xu et al.

(10) Patent No.: US 11,612,640 B2
(45) Date of Patent: Mar. 28, 2023

(54) ACYLATED GLP-1 DERIVATIVE

(71) Applicant: SCIWIND BIOSCIENCES CO., LTD., Zhejiang (CN)

(72) Inventors: Zheng Xu, Beijing (CN); Feng Li, Beijing (CN); Rui Song, Beijing (CN); Wanjun Guo, Beijing (CN); Hai Pan, Beijing (CN); Jing Feng, Beijing (CN)

(73) Assignee: SCIWIND BIOSCIENCES CO., LTD., Zhejiang (CN)

( * ) Notice: Subject to any disclaimer, the term of this patent is extended or adjusted under 35 U.S.C. 154(b) by 38 days.

(21) Appl. No.: 17/048,550

(22) PCT Filed: Apr. 19, 2019

(86) PCT No.: PCT/CN2019/083383
§ 371 (c)(1),
(2) Date: Oct. 16, 2020

(87) PCT Pub. No.: WO2019/201328
PCT Pub. Date: Oct. 24, 2019

(65) Prior Publication Data
US 2021/0393744 A1      Dec. 23, 2021

(30) Foreign Application Priority Data
Apr. 19, 2018  (WO) ................ PCT/CN2018/083789

(51) Int. Cl.
*A61K 38/00* (2006.01)
*A61K 38/26* (2006.01)
*A61K 47/54* (2017.01)
*A61P 3/10* (2006.01)

(52) U.S. Cl.
CPC ............ *A61K 38/26* (2013.01); *A61K 47/542* (2017.08); *A61P 3/10* (2018.01)

(58) Field of Classification Search
CPC ...... A61K 38/26; A61K 47/542; A61K 47/68; A61P 3/10; C07K 14/605; C07K 1/107; C07K 1/02; C07K 1/30; C07K 1/36
See application file for complete search history.

(56) References Cited

U.S. PATENT DOCUMENTS

| | | | |
|---|---|---|---|
| 8,129,343 B2 | 3/2012 | Lau | |
| 2017/0320927 A1* | 11/2017 | Sauerberg | ............... A61P 27/02 |

FOREIGN PATENT DOCUMENTS

| | | | |
|---|---|---|---|
| CN | 1882356 A | 12/2006 | |
| CN | 1938334 A | 3/2007 | |
| CN | 101133082 A | 2/2008 | |
| CN | 101367873 A | 2/2008 | |
| CN | 104411322 A | 3/2015 | |
| CN | 104519902 A | 4/2015 | |
| CN | 105377884 A | 3/2016 | |
| CN | 105451776 A | 3/2016 | |
| CN | 107033234 A | 8/2017 | |
| JP | 2010538042 A | 9/2010 | |
| JP | 2018505859 A | 3/2018 | |
| JP | 2018506507 A | 3/2018 | |
| WO | 2005023291 A2 | 3/2005 | |
| WO | 2005023291 A3 | 4/2005 | |
| WO | 2005049061 A2 | 6/2005 | |
| WO | 2005072045 A2 | 8/2005 | |
| WO | 2005049061 A3 | 10/2005 | |
| WO | 2005072045 A3 | 10/2005 | |
| WO | 2006002532 A1 | 1/2006 | |
| WO | 2006097538 A1 | 9/2006 | |
| WO | WO-2006097537 A2 * | 9/2006 | ........... C07K 14/605 |
| WO | 2009030738 A1 | 3/2009 | |
| WO | 2009030771 A1 | 3/2009 | |
| WO | 2013167454 A1 | 11/2013 | |
| WO | 2013167455 A1 | 11/2013 | |
| WO | 2015000942 A1 | 1/2015 | |
| WO | 2015022400 A1 | 2/2015 | |
| WO | WO-2015155151 A1 * | 10/2015 | ................ A61P 1/00 |
| WO | 2016083499 A1 | 6/2016 | |
| WO | 2016097108 A1 | 6/2016 | |

OTHER PUBLICATIONS

International Search Report, dated Aug. 27, 2018, for PCT Application No. PCT/CN2018/083789, 7 pages.
International Search Report, dated Jun. 27, 2019, for PCT Application No. PCT/CN2019/083383, 4 pages.
Manandhar, B. et al. (Oct. 28, 2014). "Glucagon-Like Peptide-1 (GLP-1) Analogs: Recent Advances, New Possibilities, and Therapeutic Implications," Journal of Medicinal Chemistry 28:1020-1037.
Lau, J. et al. (Aug. 26, 2015). "Discovery of c-Weekly Glucagon-Like Peptide-1(GLP-1) Analogue Semaglutide," Journal of Medicinal Chemistry 58(18):7370-7380.
Ward, B.P et al. (Nov. 1, 2013, e-pub. Sep. 5, 2013). "Peptide Lipidation Stabilizes Structure to Enhance Biological Function," Molecular Metabolism 2(4):468-479.

* cited by examiner

*Primary Examiner* — Aradhana Sasan
*Assistant Examiner* — Mercy H Sabila
(74) *Attorney, Agent, or Firm* — Morrison & Foerster LLP

(57) ABSTRACT

Provided are a GLP-1(7-37) polypeptide analogue, a fatty acid-modified derivative of the analogue, and a medicament comprising the derivative. Further, also provided are a preparation method of the derivative, and use of the same in the preparation of a medicament.

14 Claims, 4 Drawing Sheets
Specification includes a Sequence Listing.

SEQUENCE LISTING

<160> NUMBER OF SEQ ID NOS: 40

<210> SEQ ID NO 1
<211> LENGTH: 31
<212> TYPE: PRT
<213> ORGANISM: Artificial sequence
<220> FEATURE:
<223> OTHER INFORMATION: Synthetic Construct

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 31
<212> TYPE: PRT
<213> ORGANISM: Artificial sequence
<220> FEATURE:
<223> OTHER INFORMATION: Synthetic Construct

<400> SEQUENCE: 2

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Arg Gly
            20                  25                  30

<210> SEQ ID NO 3
<211> LENGTH: 93
<212> TYPE: DNA
<213> ORGANISM: Artificial sequence
<220> FEATURE:
<223> OTHER INFORMATION: Synthetic Construct

<400> SEQUENCE: 3
cacgttgaag gtaccttcac ctctgacgtt tcttcttacc tggaagaaca ggctgctaaa      60
gaattcatcg cttggctggt tcgtggtcgt ggt                                   93

<210> SEQ ID NO 4
<211> LENGTH: 31
<212> TYPE: PRT
<213> ORGANISM: Artificial sequence
<220> FEATURE:
<223> OTHER INFORMATION: Synthetic Construct

<400> SEQUENCE: 4

His Val Glu Gly Thr Phe Thr Ser Asp Val Ser Ser Lys Leu Glu Glu
1               5                   10                  15

Gln Ala Ala Arg Glu Phe Ile Ala Trp Leu Val Arg Gly Arg Gly
            20                  25                  30

<210> SEQ ID NO 5
<211> LENGTH: 93
<212> TYPE: DNA
<213> ORGANISM: Artificial sequence
<220> FEATURE:
<223> OTHER INFORMATION: Synthetic Construct

<400> SEQUENCE: 5
cacgttgaag gtaccttcac ctctgacgtt tcttctaaac tggaagaaca ggctgctcgt      60
gaattcatcg cttggctggt tcgtggtcgt ggt                                   93

<210> SEQ ID NO 6
<211> LENGTH: 31
<212> TYPE: PRT
<213> ORGANISM: Artificial sequence
<220> FEATURE:
<223> OTHER INFORMATION: Synthetic Construct

<400> SEQUENCE: 6

```
His Val Glu Gly Thr Phe Thr Ser Asp Val Ser Ser Tyr Leu Glu Glu
1               5                   10                  15

Lys Ala Ala Arg Glu Phe Ile Ala Trp Leu Val Arg Gly Arg Gly
            20                  25                  30
```

<210> SEQ ID NO 7
<211> LENGTH: 93
<212> TYPE: DNA
<213> ORGANISM: Artificial sequence
<220> FEATURE:
<223> OTHER INFORMATION: Synthetic Construct

<400> SEQUENCE: 7

```
cacgttgaag gtaccttcac ctctgacgtt tcttcttacc tggaagaaaa agctgctcgt    60
gaattcatcg cttggctggt tcgtggtcgt ggt                                 93
```

<210> SEQ ID NO 8
<211> LENGTH: 31
<212> TYPE: PRT
<213> ORGANISM: Artificial sequence
<220> FEATURE:
<223> OTHER INFORMATION: Synthetic Construct

<400> SEQUENCE: 8

```
His Val Glu Gly Thr Phe Thr Ser Asp Val Ser Ser Tyr Leu Glu Glu
1               5                   10                  15

Gln Ala Ala Arg Lys Phe Ile Ala Trp Leu Val Arg Gly Arg Gly
            20                  25                  30
```

<210> SEQ ID NO 9
<211> LENGTH: 93
<212> TYPE: DNA
<213> ORGANISM: Artificial sequence
<220> FEATURE:
<223> OTHER INFORMATION: Synthetic Construct

<400> SEQUENCE: 9

```
cacgttgaag gtaccttcac ctctgacgtt tcttcttacc tggaagaaca ggctgctcgt    60
aaattcatcg cttggctggt tcgtggtcgt ggt                                 93
```

<210> SEQ ID NO 10
<211> LENGTH: 31
<212> TYPE: PRT
<213> ORGANISM: Artificial sequence
<220> FEATURE:
<223> OTHER INFORMATION: Synthetic Construct

<400> SEQUENCE: 10

```
His Val Glu Gly Thr Phe Thr Ser Asp Val Ser Ser Tyr Leu Glu Glu
1               5                   10                  15

Gln Ala Ala Arg Glu Phe Ile Lys Trp Leu Val Arg Gly Arg Gly
            20                  25                  30
```

<210> SEQ ID NO 11
<211> LENGTH: 93
<212> TYPE: DNA

<213> ORGANISM: Artificial sequence
<220> FEATURE:
<223> OTHER INFORMATION: Synthetic Construct

<400> SEQUENCE: 11

```
cacgttgaag gtaccttcac ctctgacgtt tcttcttacc tggaagaaca ggctgctcgt    60
gaattcatca aatggctggt tcgtggtcgt ggt                                 93
```

<210> SEQ ID NO 12
<211> LENGTH: 31
<212> TYPE: PRT
<213> ORGANISM: Artificial sequence
<220> FEATURE:
<223> OTHER INFORMATION: Synthetic Construct

<400> SEQUENCE: 12

```
His Val Glu Gly Thr Phe Thr Ser Asp Val Ser Ser Tyr Leu Glu Glu
1               5                   10                  15

Gln Ala Ala Arg Glu Phe Ile Ala Trp Leu Val Lys Gly Arg Gly
            20                  25                  30
```

<210> SEQ ID NO 13
<211> LENGTH: 93
<212> TYPE: DNA
<213> ORGANISM: Artificial sequence
<220> FEATURE:
<223> OTHER INFORMATION: Synthetic Construct

<400> SEQUENCE: 13

```
cacgttgaag gtaccttcac ctctgacgtt tcttcttacc tggaagaaca ggctgctcgt    60
gaattcatcg cttggctggt taaaggtcgt ggt                                 93
```

<210> SEQ ID NO 14
<211> LENGTH: 31
<212> TYPE: PRT
<213> ORGANISM: Artificial sequence
<220> FEATURE:
<223> OTHER INFORMATION: Synthetic Construct

<400> SEQUENCE: 14

```
His Val Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Lys Gly
            20                  25                  30
```

<210> SEQ ID NO 15
<211> LENGTH: 93
<212> TYPE: DNA
<213> ORGANISM: Artificial sequence
<220> FEATURE:
<223> OTHER INFORMATION: Synthetic Construct

<400> SEQUENCE: 15

```
cacgttgaag gtaccttcac ctctgacgtt tcttcttacc tggaagaaca ggctgctcgt    60
gaattcatcg cttggctggt tcgtggtaaa ggt                                 93
```

<210> SEQ ID NO 16
<211> LENGTH: 31
<212> TYPE: PRT
<213> ORGANISM: Artificial sequence
<220> FEATURE:
<223> OTHER INFORMATION: Synthetic Construct

<400> SEQUENCE: 16

His Val Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Lys
            20                  25                  30

<210> SEQ ID NO 17
<211> LENGTH: 93
<212> TYPE: DNA
<213> ORGANISM: Artificial sequence
<220> FEATURE:
<223> OTHER INFORMATION: Synthetic Construct

<400> SEQUENCE: 17
cacgttgaag gtaccttcac ctctgacgtt tcttcttacc tggaagaaca ggctgctcgt    60
gaattcatcg cttggctggt tcgtggtcgt aaa                                  93

<210> SEQ ID NO 18
<211> LENGTH: 421
<212> TYPE: DNA
<213> ORGANISM: Artificial sequence
<220> FEATURE:
<223> OTHER INFORMATION: Synthetic Construct

<400> SEQUENCE: 18
attttgttta actttaataa ggagatatac catgcatcac catcatcacc acgctaaacc    60
ggaagttaaa ccggaagtta aaccggaaac ccacatcaac ctgaaagttt ctgacggttc   120
ttctgaaatc ttcttcaaaa tcaaaaaaac caccccgctg cgtcgtctga tggaagcttt   180
cgctaaacgt cagggtaaag aaatggactc tctgcgtttc ctgtacgacg gtatccgtat   240
ccaggctgac cagaccccgg aagacctgga catggaagac aacgacatca tcgaagctca   300
ccgtgaacag atcggtggtc acgttgaagg taccttcacc tctgacgttt cttcttacct   360
ggaagaaaaa gctgctcgtg aattcatcgc ttggctggtt cgtggtcgtg gttaataata   420
a                                                                    421

<210> SEQ ID NO 19
<211> LENGTH: 31
<212> TYPE: PRT
<213> ORGANISM: Artificial sequence
<220> FEATURE:
<223> OTHER INFORMATION: Synthetic Construct

<400> SEQUENCE: 19

His Thr Glu Gly Thr Phe Thr Ser Asp Val Ser Ser Tyr Leu Glu Glu
1               5                   10                  15

Lys Ala Ala Arg Glu Phe Ile Ala Trp Leu Val Arg Gly Arg Gly
            20                  25                  30

<210> SEQ ID NO 20
<211> LENGTH: 93
<212> TYPE: DNA
<213> ORGANISM: Artificial sequence
<220> FEATURE:
<223> OTHER INFORMATION: Synthetic Construct

<400> SEQUENCE: 20
cacaccgaag gtaccttcac ctctgacgtt tcttcttacc tggaagaaaa agctgctcgt    60
gaattcatcg cttggctggt tcgtggtcgt ggt                                  93

<210> SEQ ID NO 21

```
<211> LENGTH: 31
<212> TYPE: PRT
<213> ORGANISM: Artificial sequence
<220> FEATURE:
<223> OTHER INFORMATION: Synthetic Construct

<400> SEQUENCE: 21

His Ile Glu Gly Thr Phe Thr Ser Asp Val Ser Ser Tyr Leu Glu Glu
1               5                   10                  15
Lys Ala Ala Arg Glu Phe Ile Ala Trp Leu Val Arg Gly Arg Gly
            20                  25                  30

<210> SEQ ID NO 22
<211> LENGTH: 93
<212> TYPE: DNA
<213> ORGANISM: Artificial sequence
<220> FEATURE:
<223> OTHER INFORMATION: Synthetic Construct

<400> SEQUENCE: 22
cacattgaag gtaccttcac ctctgacgtt tcttcttacc tggaagaaaa agctgctcgt      60
gaattcatcg cttggctggt tcgtggtcgt ggt                                  93

<210> SEQ ID NO 23
<211> LENGTH: 31
<212> TYPE: PRT
<213> ORGANISM: Artificial sequence
<220> FEATURE:
<223> OTHER INFORMATION: Synthetic Construct

<400> SEQUENCE: 23

His Leu Glu Gly Thr Phe Thr Ser Asp Val Ser Ser Tyr Leu Glu Glu
1               5                   10                  15
Lys Ala Ala Arg Glu Phe Ile Ala Trp Leu Val Arg Gly Arg Gly
            20                  25                  30

<210> SEQ ID NO 24
<211> LENGTH: 93
<212> TYPE: DNA
<213> ORGANISM: Artificial sequence
<220> FEATURE:
<223> OTHER INFORMATION: Synthetic Construct

<400> SEQUENCE: 24
cacctggaag gtaccttcac ctctgacgtt tcttcttacc tggaagaaaa agctgctcgt      60
gaattcatcg cttggctggt tcgtggtcgt ggt                                  93

<210> SEQ ID NO 25
<211> LENGTH: 31
<212> TYPE: PRT
<213> ORGANISM: Artificial sequence
<220> FEATURE:
<223> OTHER INFORMATION: Synthetic Construct

<400> SEQUENCE: 25

His Gly Glu Gly Thr Phe Thr Ser Asp Val Ser Ser Tyr Leu Glu Glu
1               5                   10                  15
Lys Ala Ala Arg Glu Phe Ile Ala Trp Leu Val Arg Gly Arg Gly
            20                  25                  30

<210> SEQ ID NO 26
<211> LENGTH: 93
<212> TYPE: DNA
<213> ORGANISM: Artificial sequence
```

```
<220> FEATURE:
<223> OTHER INFORMATION: Synthetic Construct

<400> SEQUENCE: 26
caccgcgaag gtaccttcac ctctgacgtt tcttcttacc tggaagaaaa agctgctcgt    60
gaattcatcg cttggctggt tcgtggtcgt ggt                                 93

<210> SEQ ID NO 27
<211> LENGTH: 31
<212> TYPE: PRT
<213> ORGANISM: Artificial sequence
<220> FEATURE:
<223> OTHER INFORMATION: Synthetic Construct

<400> SEQUENCE: 27

His Ser Glu Gly Thr Phe Thr Ser Asp Val Ser Ser Tyr Leu Glu Glu
1               5                   10                  15

Lys Ala Ala Arg Glu Phe Ile Ala Trp Leu Val Arg Gly Arg Gly
            20                  25                  30

<210> SEQ ID NO 28
<211> LENGTH: 93
<212> TYPE: DNA
<213> ORGANISM: Artificial sequence
<220> FEATURE:
<223> OTHER INFORMATION: Synthetic Construct

<400> SEQUENCE: 28
cacagcgaag gtaccttcac ctctgacgtt tcttcttacc tggaagaaaa agctgctcgt    60
gaattcatcg cttggctggt tcgtggtcgt ggt                                 93

<210> SEQ ID NO 29
<211> LENGTH: 31
<212> TYPE: PRT
<213> ORGANISM: Artificial sequence
<220> FEATURE:
<223> OTHER INFORMATION: Synthetic Construct

<400> SEQUENCE: 29

His Thr Glu Gly Thr Phe Thr Ser Asp Val Ser Ser Tyr Leu Glu Glu
1               5                   10                  15

Gln Ala Ala Arg Glu Phe Ile Lys Trp Leu Val Arg Gly Arg Gly
            20                  25                  30

<210> SEQ ID NO 30
<211> LENGTH: 93
<212> TYPE: DNA
<213> ORGANISM: Artificial sequence
<220> FEATURE:
<223> OTHER INFORMATION: Synthetic Construct

<400> SEQUENCE: 30
cacaccgaag gtaccttcac ctctgacgtt tcttcttacc tggaagaaca ggctgctcgt    60
gaattcatca aatggctggt tcgtggtcgt ggt                                 93

<210> SEQ ID NO 31
<211> LENGTH: 31
<212> TYPE: PRT
<213> ORGANISM: Artificial sequence
<220> FEATURE:
<223> OTHER INFORMATION: Synthetic Construct

<400> SEQUENCE: 31
```

His Ile Glu Gly Thr Phe Thr Ser Asp Val Ser Ser Tyr Leu Glu Glu
1               5                   10                  15

Gln Ala Ala Arg Glu Phe Ile Lys Trp Leu Val Arg Gly Arg Gly
            20                  25                  30

<210> SEQ ID NO 32
<211> LENGTH: 93
<212> TYPE: DNA
<213> ORGANISM: Artificial sequence
<220> FEATURE:
<223> OTHER INFORMATION: Synthetic Construct

<400> SEQUENCE: 32
cacattgaag gtaccttcac ctctgacgtt tcttcttacc tggaagaaca ggctgctcgt      60
gaattcatca aatggctggt tcgtggtcgt ggt                                  93

<210> SEQ ID NO 33
<211> LENGTH: 31
<212> TYPE: PRT
<213> ORGANISM: Artificial sequence
<220> FEATURE:
<223> OTHER INFORMATION: Synthetic Construct

<400> SEQUENCE: 33

His Leu Glu Gly Thr Phe Thr Ser Asp Val Ser Ser Tyr Leu Glu Glu
1               5                   10                  15

Gln Ala Ala Arg Glu Phe Ile Lys Trp Leu Val Arg Gly Arg Gly
            20                  25                  30

<210> SEQ ID NO 34
<211> LENGTH: 93
<212> TYPE: DNA
<213> ORGANISM: Artificial sequence
<220> FEATURE:
<223> OTHER INFORMATION: Synthetic Construct

<400> SEQUENCE: 34
cacctggaag gtaccttcac ctctgacgtt tcttcttacc tggaagaaca ggctgctcgt      60
gaattcatca aatggctggt tcgtggtcgt ggt                                  93

<210> SEQ ID NO 35
<211> LENGTH: 31
<212> TYPE: PRT
<213> ORGANISM: Artificial sequence
<220> FEATURE:
<223> OTHER INFORMATION: Synthetic Construct

<400> SEQUENCE: 35

His Gly Glu Gly Thr Phe Thr Ser Asp Val Ser Ser Tyr Leu Glu Glu
1               5                   10                  15

Gln Ala Ala Arg Glu Phe Ile Lys Trp Leu Val Arg Gly Arg Gly
            20                  25                  30

<210> SEQ ID NO 36
<211> LENGTH: 93
<212> TYPE: DNA
<213> ORGANISM: Artificial sequence
<220> FEATURE:
<223> OTHER INFORMATION: Synthetic Construct

<400> SEQUENCE: 36
cacggcgaag gtaccttcac ctctgacgtt tcttcttacc tggaagaaca ggctgctcgt      60
gaattcatca aatggctggt tcgtggtcgt ggt                                  93

<210> SEQ ID NO 37
<211> LENGTH: 31
<212> TYPE: PRT
<213> ORGANISM: Artificial sequence
<220> FEATURE:
<223> OTHER INFORMATION: Synthetic Construct

<400> SEQUENCE: 37

His Ser Glu Gly Thr Phe Thr Ser Asp Val Ser Ser Tyr Leu Glu Glu
1               5                   10                  15

Gln Ala Ala Arg Glu Phe Ile Lys Trp Leu Val Arg Gly Arg Gly
            20                  25                  30

<210> SEQ ID NO 38
<211> LENGTH: 93
<212> TYPE: DNA
<213> ORGANISM: Artificial sequence
<220> FEATURE:
<223> OTHER INFORMATION: Synthetic Construct

<400> SEQUENCE: 38
cacagcgaag gtaccttcac ctctgacgtt tcttcttacc tggaagaaca ggctgctcgt      60
gaattcatca aatggctggt tcgtggtcgt ggt                                   93

<210> SEQ ID NO 39
<211> LENGTH: 31
<212> TYPE: PRT
<213> ORGANISM: Artificial sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = V, T, I, L, G or S
<220> FEATURE:
<221> NAME/KEY: VARIANT
<222> LOCATION: 13
<223> OTHER INFORMATION: Xaa = Y or K
<220> FEATURE:
<221> NAME/KEY: VARIANT
<222> LOCATION: 17
<223> OTHER INFORMATION: Xaa = Q or K
<220> FEATURE:
<221> NAME/KEY: VARIANT
<222> LOCATION: 21
<223> OTHER INFORMATION: Xaa = E or K
<220> FEATURE:
<221> NAME/KEY: VARIANT
<222> LOCATION: 24
<223> OTHER INFORMATION: Xaa = A or K
<220> FEATURE:
<221> NAME/KEY: VARIANT
<222> LOCATION: 28
<223> OTHER INFORMATION: Xaa = R or K
<220> FEATURE:
<221> NAME/KEY: VARIANT
<222> LOCATION: 30
<223> OTHER INFORMATION: Xaa = R or K
<220> FEATURE:
<221> NAME/KEY: VARIANT
<222> LOCATION: 31
<223> OTHER INFORMATION: Xaa = G or K

<400> SEQUENCE: 39

His Xaa Glu Gly Thr Phe Thr Ser Asp Val Ser Ser Xaa Leu Glu Glu
1               5                   10                  15

Xaa Ala Ala Arg Xaa Phe Ile Xaa Trp Leu Val Xaa Gly Xaa Xaa
            20                  25                  30

```
<210> SEQ ID NO 40
<211> LENGTH: 30
<212> TYPE: PRT
<213> ORGANISM: Artificial sequence
<220> FEATURE:
<223> OTHER INFORMATION: Synthetic Construct
<220> FEATURE:
<221> NAME/KEY: VARIANT
<222> LOCATION: 1, 2
<223> OTHER INFORMATION: positions 1 and 2 are linked by Semaglutide
      (Aib)

<400> SEQUENCE: 40

His Gly Thr Phe Thr Ser Asp Val Ser Ser Tyr Leu Glu Gly Gln
1               5                   10                  15

Ala Ala Lys Glu Phe Ile Ala Trp Leu Val Arg Gly Arg Gly
            20                  25                  30
```

ACYLATED GLP-1 DERIVATIVE

CROSS REFERENCE TO RELATED APPLICATIONS

This application is a National Phase application under 35 U.S.C. § 371 of International Application No. PCT/CN2019/083383, filed Apr. 19, 2019, which claims priority to International Application No. PCT/CN2018/083789, filed Apr. 19, 2018, the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 794922002100SUB2SEQLIST.TXT, date recorded: Apr. 20, 2022, size: 14,242 KB).

FIELD OF THE INVENTION

The present invention belongs to the field of polypeptide technology. In particular, the present invention relates to fatty acid modified derivatives of GLP-1(7-37) polypeptide analogues. In addition, the invention also relates to a preparation method of the peptide derivative, a medicament comprising the peptide derivative, and use thereof in the preparation of the medicament.

BACKGROUND OF THE INVENTION

Diabetes is a glucose metabolism disorder, caused by genetic and environmental factors. It has become the third major disease after tumors, cardiovascular and cerebrovascular diseases, that threatens human health and life safety. Diabetes itself does not necessarily cause harm, but long-term high levels of blood glucose will damage large blood vessels and micro-vessels and endanger the heart, brain, kidney, peripheral nerves, eyes, feet, etc. According to statistics of the World Health Organization, there are more than 100 diabetes complications, which is a disease with the most known complications. More than half of the deaths due to diabetes are caused by cardiovascular and cerebrovascular diseases, and 10% are caused by nephropathy. Amputation due to diabetes is 10-20 times that of non-diabetes. Therefore, the treatment of diabetes and the prevention of its complications are vital social issues.

Diabetes may be divided into several types due to different pathogenesis. Most of them belong to type II diabetes (about 90%), mainly due to overweight and lack of physical activity. Type II diabetes patients often have abnormalities in insulin resistance and insufficient insulin secretion, and islet β-cell apoptosis often occurs in the middle and late stages of the disease. At present, the action mechanism of oral hypoglycemic drugs used in clinic is mostly to enhance insulin sensitivity or promote insulin secretion to stabilize blood glucose, which cannot solve the problem of R cell apoptosis. The medicaments of glucagon-like peptide-1 (GLP-1) and its analogue have the effect of slowing down the apoptosis of β cells, promoting their regeneration, and promoting the differentiation and proliferation of islet β cells, thereby making it a research focus for the treatment of type II diabetes.

In 1983, Bell et al. found glucagon-like peptide-1 (GLP-1) when analyzing the gene sequence of proglucagon (PG) (Bell G I., Sanchez-Pescador R., Laybourn P. J., et al., Exon duplication and divergence in the human preproglucagon gene [J]. Nature, 1983, 304(5924): 368-371). The PG gene sequence consists of 6 exons and 5 introns, comprising 3 main domains: glucagon (33-61), GLP-1 (72-108), and GLP-2 (126-158). The mRNA of PG is expressed in pancreatic A cells, intestinal L cells and brain, and specific translation modification is carried out in these tissue cells to form different final products.

There are two subtypes of GLP, GLP-1 analogue and GLP-2 analogue. They have nearly half the same amino acid sequence as glucagon, and there is also about 35% homology between the two. GLP-1 analogue is a polypeptide hormone secreted by Langerhans' cells of terminal jejunum, ileum and colon, having multiple functions such as glucose-dependent promotion of insulin secretion and biosynthesis, inhibition of glucagon secretion and gastric emptying. GLP-2 analogue is synthesized in the intestinal tissue, and neurons in the brain stem and hypothalamus of the central nervous system, and mainly promotes normal growth of small intestine and repair of intestinal mucosal damage (Fu Gang, Gong Min, Xu Weiren; Research progress of glucagon-like peptide 1 and its receptor agonists [J]. Tianjin Medical Journal, 2012, 40(2):181-184).

GLP-1 is an endogenous hormone that promotes insulin secretion, mainly secreted by intestinal L-cells, and plays a role in balancing insulin and glucose levels.

The primary structure of GLP-1 is: histidine (His)-alanine (Ala)-glutamic acid (Glu)-phenylalanine (Phe)-glutamic acid (Glu)-arginine (Arg)-histidine (His)-alanine (Ala)-glutamic acid (Glu)-glycine (Gly)-threonine (Thr)-phenylalanine (Phe)-threonine (Thr)-Serine (Ser)-aspartic acid (Asp)-Valine (Val)-Serine (Ser)-Serine (Ser)-tyrosine (Tyr)-leucine (Leu)-glutamic acid (Glu)-glycine (Gly)-glutamine (Gln)-alanine (Ala)-alanine (Ala)-lysine (Lys)-glutamic acid (Glu)-phenylalanine (Phe)-isoleucine (Ile)-alanine (Ala)-tryptophan (Trp)-leucine (Leu)-valine (Val)-lysine (Lys)-glycine (Gly)-arginine (Arg)-glycine (Gly). DDP-IV may rapidly degrade histidine (H)-alanine (A) at positions 7-8 at the N-terminus. DDP-IV mainly mediated hydrolysis for peptide chain end, wherein the position 8 is alanine or proline, the enzyme will degrade it and cause GLP-1 to lose its activity rapidly (Aertgeerts K, Ye S, Tennant M, Q et al., Crystal structure of human dipeptidyl peptidase IV in complex with a dipeptide peptidase reveals details on substrate specificity and tetrahedral intermediate [J]. Protein Sci., 2004, 13(2):412-421). Sarrauste De Menthiere et al. proposed a GLP-1 models to observe the changes in affinity with receptor and intrinsic activity of GLP-1 analogues by amino acid substitution. The histidine at position 7 is the determinant of affinity and intrinsic activity, the aromatic ring of histidine is smaller than that of tryptophan, and there is no polar substituent; the side chain of the alanine at position 8 has a polar group that affects the activity of GLP-1; the size of the side chain should not be too large, when it exceeds a certain limit, the activity will decrease; when the glutamic acid at position 9 is replaced by certain amino acids, such as acidic, polar and hydrophobic amino acids, the activity will not change, however the activity will decrease or even lost when it is replaced by basic amino acids. Once GLP-1 is bound to its receptor, a ring structure in between the amino acids of positions 7-15 is formed with ionic bond and Ala8-Glu9-Gly10-Thr11 will form a β-turn, those confirmational change will make three aromatic nuclei such as the histidine of position 7, the phenylalanine of position 12, and the tyrosine of position 19 interact with each other, corresponding to the hydrophobic pockets of the aromatic clusters present on the receptor; they are speculated to activate the receptor; the glycine at position 22 is a flexible amino acid, which acts as a flexible linker, maintaining a spiral curl. Destroying glycine will cause all aromatic amino acids to cluster, resulting in the affinity with the receptor is reduced by 1/40 (Sarauste De Menthierec, Chavanieua, Grassyg, et al. Structural requirements of the N-terminal region of GLP-1-[7-37]—NH$_2$ for receptor interaction and cAMP production [J]. Eur J Med Chem, 2004, 39(6):473-480).

GLP-1 includes GLP-1(1-37), GLP-1(1-36), GLP-1(7-37) glycine derivatives and GLP-1 (7-36) NH$_2$ and other molecular forms. It is generally believed that the latter two have the same biological activity. GLP-1 (1-37) secreted by intestinal mucosa L cells is inactive, and it requires further hydrolyze and excise the 6 amino acids at the N-terminal to become active GLP-1(7-37). GLP-1(7-37) exists in the body for a relatively short time, and is quickly degraded. Therefore, various studies have been conducted on GLP-1 analogues with anti-DPP IV function. For example, U.S. Pat. No. 5,545,618 describes modification of N-terminus with an alkyl or acyl group, and Gallwitz et al. describes N-methylation or a-methylation of His at position 7, or substitution of the entire His with imidazole to increase resistance to DPP-IV and maintain physiological activity.

In addition to these modifications, the GLP-1 analogue exendin-4 (U.S. Pat. No. 5,424,686) purified from the salivary glands of the Gila lizard (*Heloderma suspectum*) has resistance to DPP IV and higher physiological activity than GLP-1. Therefore, it has an in vivo half-life of 2-4 hours which is longer than that of GLP-1. However, it's only applicable to method of increasing DPP IV resistance is applied, the physiological activity cannot be sufficiently maintained, and in the case of using commercially available exendin-4 (exenatide), it needs to be injected to the patient twice a day, which is still very painful to the patient.

These insulinotropic peptides have very small molecular weights and are therefore quickly be cleared out by the kidneys. Some scientists use chemical methods to add highly soluble polymers (such as polyethylene glycol) to the surface of the peptide to inhibit kidney clearance. For example, U.S. Pat. No. 692464 describes the binding of PEG to the lysine residue of exenatin-4 which increases the residence time in the body. However, although this method increases the residence time of peptide medicaments in the body, it also increases the molecular weight, the concentration of the peptide medicament decreases significantly, and the reactivity to the peptides also decreases.

In addition, there are a series of other methods for modifying the structure of glucagon-like peptide-1 compounds in attempt to extend the duration of their effects. For example, WO96/29342 discloses peptide hormone derivatives modified by introducing a lipophilic substituent at the C-terminal amino acid residue or N-terminal amino acid residue of the parent peptide hormone. WO98/08871 discloses a GLP-1 derivative (liraglutide) in which at least one amino acid residue of the parent peptide is linked to a lipophilic substituent. WO99/43708 discloses derivatives of GLP-1(7-35) and GLP-1(7-36) having lipophilic substituents attached to the C-terminal amino acid residue. WO00/34331 discloses double-acylated GLP-1 analogues. WO 00/69911 discloses activated insulinotropic peptides for injection, and it is believed that in patients they react with blood components to form conjugates, prolonging the duration of effect in the body.

WO2006/097537 discloses another acylated GLP-1 analogue (Semaglutide), by mutating the amino acid at position 8 to prolong the half-life as compared with the acylated GLP-1 (Liraglutide) in WO98/08871.

WO02/046227 discloses the preparation of fusion proteins by combining GLP-1, exendin-4 or its analogues with human serum albumin or immunoglobulin region (Fc) by using genetic recombination technology, this may solve the problems such as low yield and non-specificity of PEGylation, but their effect of increasing half-life in the blood is still not as significant as expected. In terms of the comprehensive glucose-lowering effect, the expected effect is not achieved, and it is not even as good as Semaglutide. In order to prolong the half-life in the blood, people have tried to use various types of peptide linkers, but the problem of this method is that it may cause an immune response.

CN107033234A discloses a fatty acid-modified conjugate of GLP-1 analogue. The fatty acid modification site is at Lys$^{26}$. Early animal experiments show that its glucose-lowering effect is superior to Semaglutide. This method may appropriately prolong the in vivo action time of GLP-1 analogues, but the plasma half-life is still not ideal.

The currently approved GLP-1 medicaments on the market mainly include exenatin-4 isolated from lizard saliva, and human-derived GLP-1 analogues either modified with fatty acids, or fused with Fc or human serum albumin. The half-life of exenatin-4 is too short (only 2-4 hours), and twice-daily injections are required. Fatty acid-modified liraglutide from Novo Nordisk is the most effective medicament in glycated hemoglobin (HbA1c) reduction with less side effects, however, as the half-life is only 13 hours and once-daily administration is required. In order to further extend the half-life in vivo and reduce the frequency of administration, in recent years, amino acid sequence mutants and long-acting GLP-1 analogues modified by Fc, fatty acids, or albumin etc. have been developed, for example, dulaglutide from Eli Lilly and Company, and Semaglutide from Novo Nordisk. The half-life of these long-acting GLP-1 analogues in the human body may be extended to various degrees, and the administration frequency of once-weekly may be achieved as the maximum long-acting effect.

After long-term research, the inventors of the present application have developed a new GLP-1 analogue and its derivatives, under the same experimental conditions they have equivalent in vitro activity as compared with Semaglutide, which being recognized as best medicament currently; in both normal mouse and diabetic mouse models, the duration of glucose-lowering effect in vivo may be increased by about 1 times, it means that in humans the dosing frequency of at least once-weekly, even biweekly, or longer intervals may be achieved. Moreover, when the dosage is 1/10 of that of Semaglutide, its glucose-lowering effect is compatible with Semaglutide, thereby having a better application prospect.

SUMMARY OF THE INVENTION

The object of the present invention is to provide a new GLP-1(7-37) analogue, and an acylated derivative of the analogue. In addition, the present invention also provides a method for preparing the analogue or derivative, a pharmaceutical composition and product containing the analogue or derivative, and their use in the prevention and treatment of diseases.

Particularly, in one aspect, the present invention provides a derivative of a GLP-1(7-37) analogue or a pharmaceutically acceptable salt thereof, wherein the GLP-1 analogue comprises a peptide consisting of an amino acid sequence with the following formula:

HX$_8$EGTFTSDVSSX$_{19}$LEEX$_{23}$AARX$_{27}$FIX$_{30}$WLVX$_{34}$GX$_{36}$X$_{37}$
(SEQ ID NO:39), wherein X$_8$ is selected from V, T, I, L, G or S; X$_{19}$ is Y or K; X$_{23}$ is Q or K; X$_{27}$ is E or K; X$_{30}$ is A or K; X$_{34}$ is R or K; X$_{36}$ is R or K; and X$_{37}$ is G or K;

provided that only one of X$_{19}$, X$_{23}$, X$_{27}$, X$_{30}$, X$_{34}$, X$_{36}$ or X$_{37}$ is a K residue, and the derivative comprises an extension portion linked to the K residue of the GLP-1(7-37) analogue, wherein the extension portion is

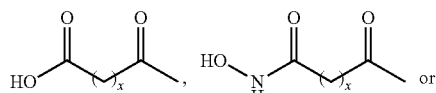 or

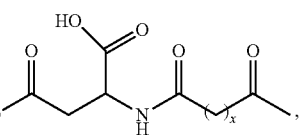

wherein x is an integer selected from 4 to 38.

Wherein the extension portion is preferably: HOOC(CH$_2$)$_{14}$CO—, HOOC(CH$_2$)$_{15}$CO—, HOOC(CH$_2$)$_{16}$CO—, HOOC(CH$_2$)$_{17}$CO—, HOOC(CH$_2$)$_{18}$CO—, HOOC(CH$_2$)$_{19}$CO—, HOOC(CH$_2$)$_{20}$CO—, HOOC(CH$_2$)$_{21}$CO—, and HOOC(CH$_2$)$_{22}$CO—; more preferably HOOC(CH$_2$)$_{16}$CO—.

In a preferred embodiment, the extension portion of the derivative of the GLP-1 analogue or a pharmaceutically acceptable salt thereof according to the invention is linked to the K residue of the GLP-1 through a linker. The linker comprises any one of the following structures:

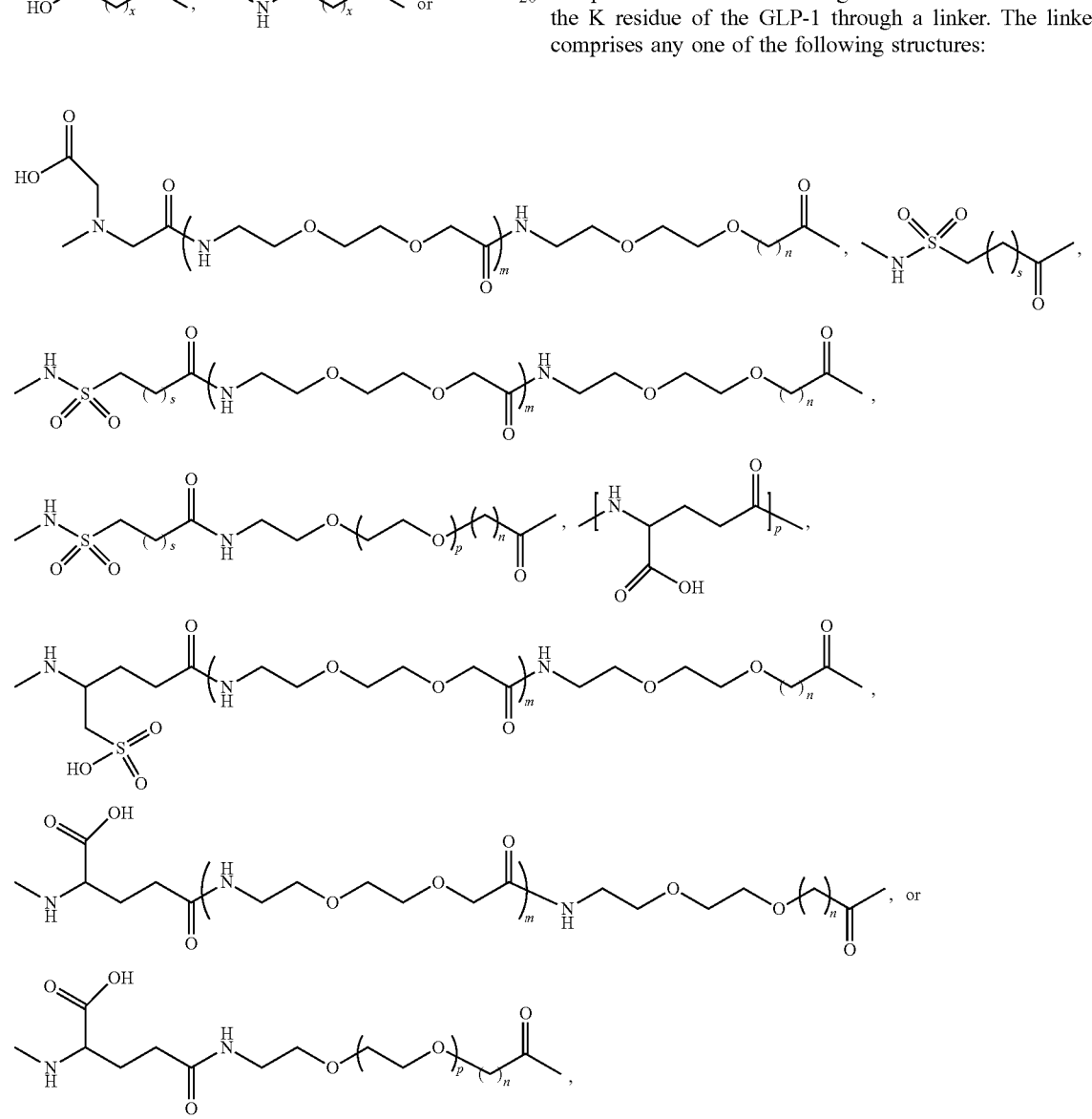

wherein m is 0, 1, 2, or 3; n is 1, 2, or 3; s is any integer selected from 0 to 6; and p is any integer selected from 1 to 8.

Preferably, the linker is:

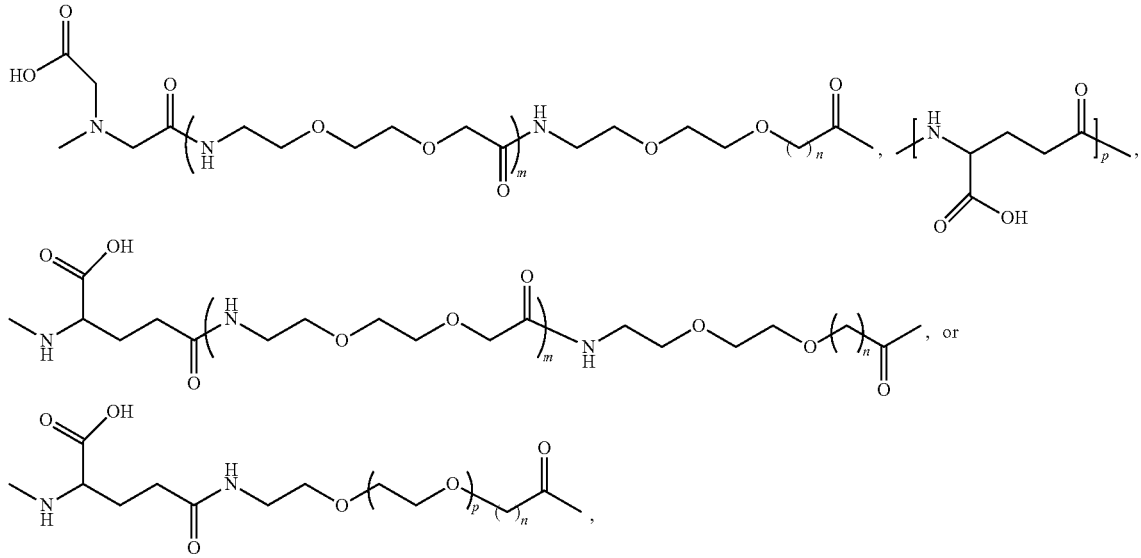

wherein m is 1 or 2; n is 1 or 2; and p is any integer selected from 1 to 5.

More preferably: the linker is:

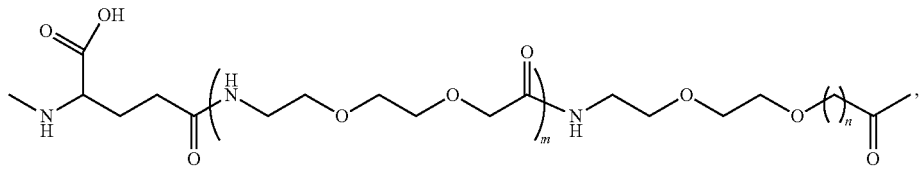

wherein m is 1, and n is 1 or 3.

The invention also relates to a GLP-1(7-37) analogue, comprising the sequence of:

$HX_8EGTFTSDVSSX_{19}LEEX_{23}AARX_{27}FIX_{30}WLVX_{34}GX_{36}X_{37}$ (SEQ ID NO: 39), which contains mutations selected from one or more of the following positions:

positions 8, 19, 23, 27, 30, 34, 36 and 37. In a preferred embodiment, the amino acid residue at position 8 is selected from V, T, I, L, G or S; the amino acid residue at position 19 is Y or K; the amino acid residue at position 23 is Q or K; the amino acid residue at position 27 is E or K; the amino acid residue at position 30 is A or K; the amino acid residue at position 34 is R or K; the amino acid residue at position 36 is R or K; the amino acid residue at position 37 is G or K; provided that only one of positions 19, 23, 27, 30, 34, 36, or 37 is a K residue In vitro binding activity of the acylated derivatives of the above GLP-1 analogues shows that the binding affinity to the GLP-1R receptor is greater than that of Semaglutide or M0 (Lys at position 26, disclosed in CN107033234A). In vivo glucose-lowering experiment also proves that, compared with the acylated GLP-1 product Semaglutide, the acylated derivatives of the above GLP-1 analogues may obtain longer duration of glucose-lowering effect in normal mice; in diabetic mice, the above derivatives have significantly better glucose-lowering and glucose tolerance-enhancing effects than Semaglutide, and when the dose is only 1/10 of that of Semaglutide or M0, its glucose-lowering effect is compatible with that of Semaglutide or M0. At the same time, the research of the present invention proves that the derivatives of the above GLP-1(7-37) analogues have better resistance to enzymatic degradation as compared with the commercially available Semaglutide.

Particularly, the present invention relates to:

1. A derivative of a GLP-1(7-37) analogue or a pharmaceutically acceptable salt thereof, wherein the GLP-1(7-37) analogue comprises an amino acid sequence of the following formula:

$HX_8EGTFTSDVSSX_{19}LEEX_{23}AARX_{27}FIX_{30}WLVX_{34}GX_{36}X_{37}$ (SEQ ID NO:39), wherein $X_8$ is selected from V, T, I, L, G or S; $X_{19}$ is Y or K; $X_{23}$ is Q or K; $X_{27}$ is E or K; $X_{30}$ is A or K; $X_{34}$ is R or K; $X_{36}$ is R or K; and $X_{37}$ is G or K;

provided that only one of $X_{19}$, $X_{23}$, $X_{27}$, $X_{30}$, $X_{34}$, $X_{36}$ or $X_{37}$ is a K residue, and the derivative comprises an extension portion linked to the K residue of the GLP-1(7-37) analogue, wherein the extension portion is

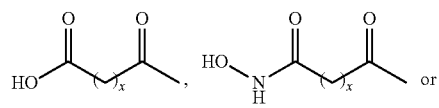

-continued

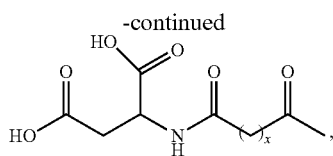

wherein x is an integer selected from 4 to 38.

2. The derivative or a pharmaceutically acceptable salt thereof according to claim 1, wherein the extension portion is selected from:

HOOC(CH$_2$)$_{14}$CO—, HOOC(CH$_2$)$_{15}$CO—, HOOC(CH$_2$)$_{16}$CO—, HOOC(CH$_2$)$_{17}$CO—, HOOC(CH$_2$)$_{18}$CO—, HOOC(CH$_2$)$_{19}$CO—, HOOC(CH$_2$)$_{20}$CO—, HOOC(CH$_2$)$_{21}$CO—, and HOOC(CH$_2$)$_{22}$CO—.

3. The derivative or a pharmaceutically acceptable salt thereof according to claim 1 or 2, wherein the extension portion is linked to the K residue of the GLP-1(7-37) analogue through a linker.

4. The derivative or a pharmaceutically acceptable salt thereof according to claim 3, wherein the linker is:

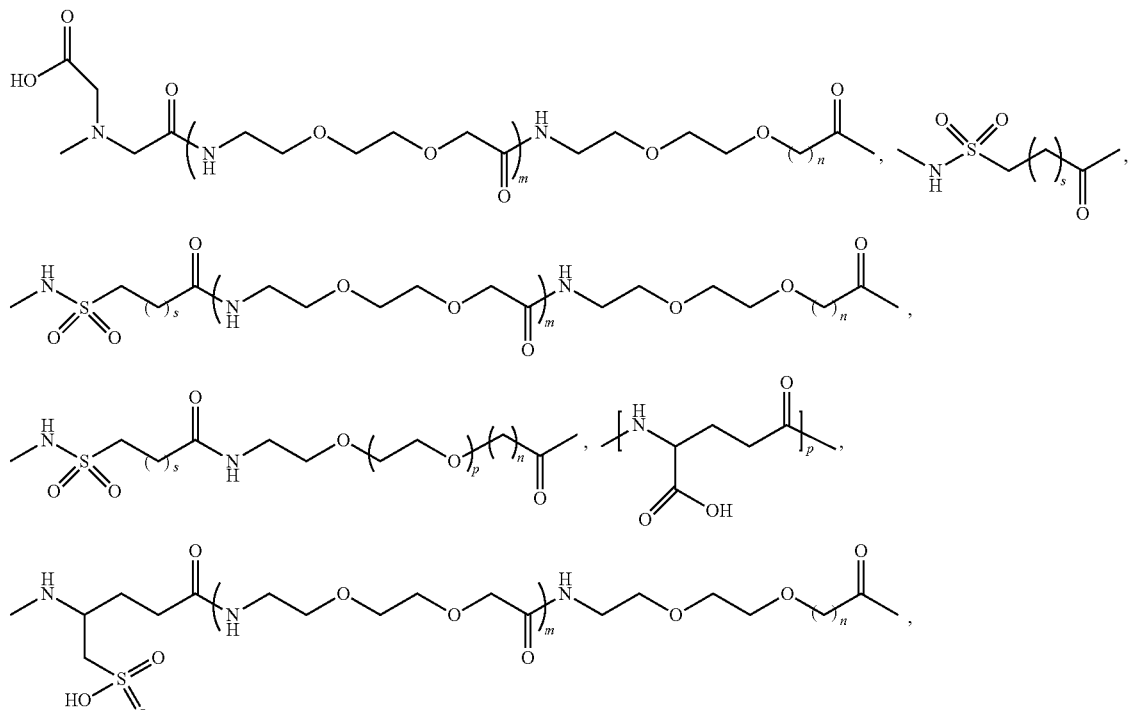

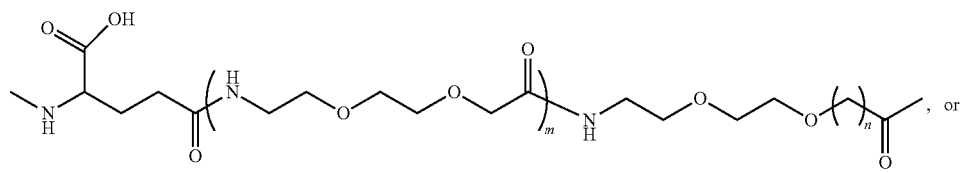, or

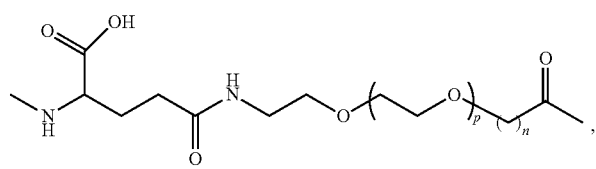, wherein m is 0, 1, 2 or 3; n is 1, 2 or 3; s is any integer selected from 0 to 6; and p is any integer selected from 1 to 8.

Preferably, the linker is:

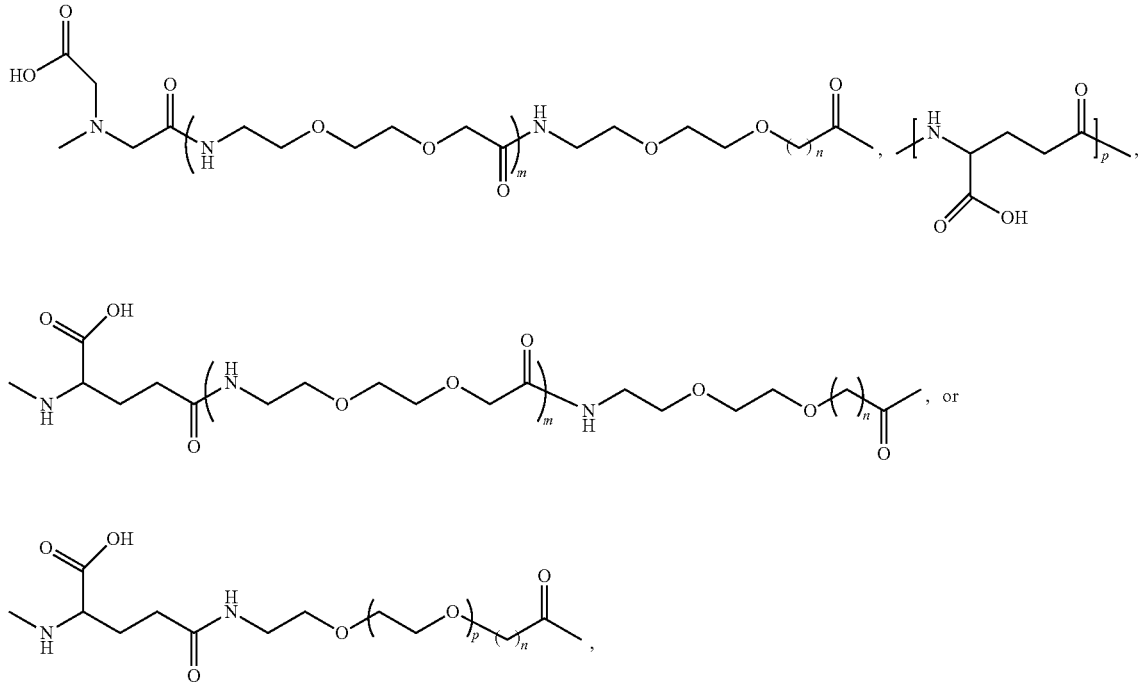

wherein m is 1 or 2; n is 1 or 2; and p is any integer selected from 1 to 5.

5. The derivative or a pharmaceutically acceptable salt thereof according to claim 4, wherein the linker is:

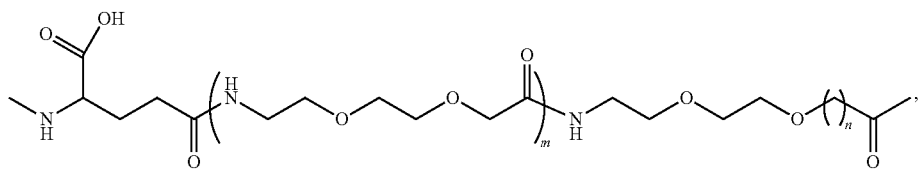

and wherein m is 1, and n is 1 or 2.

6. The derivative or a pharmaceutically acceptable salt thereof according to any one of claims 1-5, which is any derivative selected from the group consisting of: N-$\varepsilon^{23}$-[2-(2-[2-(2-[2-(2-[4-(17-carboxyheptadecanoylamino)-4(s)-carboxybutyrylamino]ethoxy)ethoxy]acetyl amino)ethoxy]ethoxy)acetyl](Val$^8$Glu$^{22}$Lys$^{23}$Arg$^{26,34}$-GLP-1(7-37)) peptide (M2), N-$\varepsilon^{30}$-[2-(2-[2-(2-[2-(2-[4-(17-carboxyheptadecanoylamino)-4(s)-carboxybutyrylamino]ethoxy)ethoxy] acetyl amino)ethoxy]ethoxy)acetyl](Val$^8$Glu$^{22}$Lys$^{30}$Arg$^{26,34}$-GLP-1(7-37)) peptide (M4), N-$\varepsilon^{34}$-[2-(2-[2-(2-[2-(2-[4-(17-carboxyheptadecanoylamino)-4(s)-carboxybutyrylamino]ethoxy)ethoxy]acetyl amino)ethoxy]ethoxy)acetyl](Val$^8$Glu$^{22}$Arg$^{26}$Lys$^{34}$-GLP-1(7-37)) peptide (M5), N-$\varepsilon^{37}$-[2-(2-[2-(2-[2-(2-[4-(17-carboxyheptadecanoylamino)-4(s)-carboxybutyrylamino]ethoxy)ethoxy]acetylamino)ethoxy]ethoxy)acetyl])(Val$^8$Glu$^{22}$Arg$^{26,34}$Lys$^{37}$-GLP-1(7-37)) peptide (M7), N-$\varepsilon^{23}$-[2-(2-[2-(2-[2-(2-[4-(17-carboxyheptadecanoylamino)-4(s)-carboxybutyrylamino]ethoxy)ethoxy]acetyl]amino)ethoxy]ethoxy)acetyl](Ile$^8$Glu$^{22}$Lys$^{23}$Arg$^{26,34}$-GLP-1(7-37)) peptide (M9) N-$\varepsilon^{30}$-[2-(2-[2-(2-[2-(2-[4-(17-carboxyheptadecanoylamino)-4(s)-carboxybutyrylamino]ethoxy)ethoxy]acetylamino)ethoxy]ethoxy)acetyl](Thr$^8$Gu$^{22}$Lys$^{30}$Arg$^{26,34}$-GLP-1(7-37)) peptide (M13) N-$\varepsilon^{30}$-[2-(2-[2-(2-[2-(2-[4-(17-carboxyheptadecanoylamino)-4(s)-carboxybutyrylamino]ethoxy)ethoxy]acetylamino)ethoxy]ethoxy)acetyl](Ile$^8$Glu$^{22}$Lys$^{30}$Arg$^{26,34}$-GLP-1(7-37)) peptide (M14), or a pharmaceutically acceptable salt thereof.

7. A method for preparing the derivative or a pharmaceutically acceptable salt thereof according to any one of claims 1-6, comprising:

(1) mixing a solution in which the GLP-1 analogue according to any one of the preceding claims is dissolved with a solution in which the extension portion according to any one of the preceding claims is dissolved;

(2) adjusting the pH to 4-5 to quench the reaction, standing until a precipitate is generated, and then collecting the precipitate; and (3) adding TFA to the precipitate, and adjusting the pH to 7.5-8.5 to quench the reaction.

8. The method according to claim 7, further comprising: adding triethylamine to a solution in which the GLP-1 analogue is dissolved, followed by mixing with a solution in which the extension portion according to any one of the preceding claims is dissolved.

9. The method according to claim 7 or 8, wherein the solution of the extension portion according to any of the preceding claims is dissolved by acetonitrile.

10. A pharmaceutical composition, comprising the derivative or a pharmaceutically acceptable salt thereof according to any one of claims 1-6, and a pharmaceutically acceptable excipient.

11. Use of the derivative or a pharmaceutically acceptable salt thereof according to any one of claims 1-6 in the preparation of a medicament for preventing and/or treating diabetes (including type I diabetes and type II diabetes) or diabetic complications.

12. The use according to claim 11, wherein the diabetic complication is diabetic nephropathy.

13. Use of the derivative or a pharmaceutically acceptable salt thereof according to any one of claims 1-6 in the preparation of a medicament for reducing blood glucose, increasing glucose tolerance, reducing islet p-cell apoptosis, enhancing islet 3-cell function, increasing islet 3-cell number, and/or restoring islet p-cell glucose sensitivity.

14. The use according to claim 13, wherein said reducing blood glucose includes reducing fasting blood glucose and/or postprandial blood glucose.

15. A method for preventing and/or treating diabetes (including type I diabetes and type II diabetes) or diabetic complications, comprising: administering prophylactically or therapeutically effective amount of the derivative or a pharmaceutically acceptable salt thereof according to any one of claims 1-6 to a subject.

16. The method according to claim 15, wherein the diabetic complication is diabetic nephropathy.

17. A method for reducing blood glucose, increasing glucose tolerance, reducing islet p-cell apoptosis, enhancing islet 3-cell function, increasing islet 3-cell number, and/or restoring islet p-cell glucose sensitivity, comprising: administering therapeutically effective amount of the derivative or a pharmaceutically acceptable salt thereof according to any one of claims 1-6 to a subject.

18. The use according to claim 17, wherein said reducing blood glucose includes reducing fasting blood glucose and/or postprandial blood glucose.

19. A GLP-1(7-37) analogue, comprising a polypeptide consisting of the following amino acid sequence:

$HX_8EGTFTSDVSSX_{19}LEEX_{23}AARX_{27}FIX_{30}WLVX_{34}GX_{36}X_{37}$
(SEQ ID NO:39), wherein $X_8$ is selected from V, T, I, L, Q or S; $X_{19}$ is Y or K; $X_{23}$ is Q or K; $X_{27}$ is E or K; $X_{30}$ is A or K; $X_{34}$ is R or K; $X_{36}$ is R or K; $X_{37}$ is G or K; and only one of $X_{19}$, $X_{23}$, $X_{26}$, $X_{27}$, $X_{30}$, $X_{34}$, $X_{36}$, or $X_{37}$ is K.

20. A pharmaceutical composition, comprising the analogue according to claim 19.

21. Use of the analogue according to claim 19 in the preparation of a medicament for preventing or treating diabetes and diabetic complications.

22. A product comprising: a container in which the pharmaceutical composition according to claim 10 or 20 is contained, and a package insert, wherein the package insert contains instructions for use of the pharmaceutical composition.

23. The product according to claim 22, further comprising a container containing one or more other medicaments.

24. The product according to claim 23, wherein the one or more other medicaments are other medicaments for treating diabetes or diabetic complications.

"Fasting blood glucose" refers to the blood glucose value determined when the subject (e.g., human) fasts, for example, the blood glucose value measured after overnight fasting, fasting (without any food, except drinking water) for at least 6 hours, such as 6-8 hours, 8-10 hours.

"Postprandial blood glucose" refers to the blood glucose value determined after a meal, for example, the blood glucose value measured 15 minutes to 2 hours, 30 minutes to 2 hours, 1 hour to 2 hours, or 2 hours after a meal.

One aspect of the present invention relates to a method for preparing a GLP-1(7-37) analogue, which includes expression of peptide by a host cell containing DNA sequence encoding the polypeptide under conditions allowing peptide expression, and then recovering the resulting peptide.

The medium used to culture the cells may be any conventional medium used to culture the host cells, e.g., a basal medium or a complex medium containing suitable additives. A suitable culture medium may be obtained from a commercial market, or a suitable culture medium may be prepared according to a disclosed preparation method. The polypeptide produced by the host cells may then be recovered from the culture medium by conventional methods, for example, the protein component in the supernatant or filtrate is precipitated with a salt such as ammonium sulfate, and is further purified by various chromatographic methods such as ion-exchange column chromatography, gel filtration chromatography, affinity chromatography, etc. according to the type of peptides.

The above coding DNA sequence may be inserted into any suitable vector. Generally, the choice of vector often depends on the host cell to which the vector is to be introduced. Therefore, the vector may be an autonomously replicating vector, i.e., a vector existing as an extrachromosomal entity, and its replication does not depend on chromosomal replication, such as a plasmid. Alternatively, the vector may be of a type that when introduced into a host cell, it will integrate into the genome of the host cell and replicate together with the chromosome which it is integrated.

The vector is preferably an expression vector in which the DNA sequence encoding the peptide is operatively linked to other segments required for transcription of the DNA (such as a promoter). Examples of promoters suitable for directing the transcription of DNA encoding the peptides of the present invention in various host cells are well known in the art, for example, see Sambrook, J, Fritsch, E F and Maniatis, T, Molecular Cloning: A Laboratory Manual, Cold Spring Harbor Laboratory Press, New York, 1989.

The vector may also contain a selection marker, such as a gene whose gene product will make up for a defect in the host cell, or may confer resistance to medicaments such as ampicillin, doxorubicin, tetracycline, chloramphenicol, neomycin, streptomycin, or methotrexate, etc.

In order to introduce the peptide expressed by the present invention into the secretory pathway of the host cell, a secretion signal sequence (also called a leader sequence) may be provided in the recombinant vector. The secretory signal sequence is linked to the DNA sequence encoding the peptide in the correct reading frame. The secretory signal sequence is usually located at the 5' terminus of the DNA sequence encoding the peptide. The secretion signal sequence may be a secretion signal sequence normally linked to the peptide, or may be derived from a gene encoding another secreted protein.

The method for separately connecting the DNA sequence encoding the peptide of the present invention, the promoter, and the optional terminator, and/or the secretion signal peptide sequence, and inserting it into a suitable vector containing the information necessary for replication, is known for the skilled person in the art.

The host cell into which the DNA sequence or recombinant vector will be introduced may be any cell capable of producing the peptide of the present invention, including bacteria, yeast, fungi, and higher eukaryotic cells. Examples of suitable host cells which are well known and used by those skilled in the art include, but are not limited to: *E. coli, S. cerevisiae*, or mammalian BHK or CHO cell lines.

The present invention relates to a medicament or a pharmaceutical composition containing the above GLP-1(7-37) analogue, and also relates to use of the analogue in the preparation of a medicament, for example, use in the preparation of a medicament in treating or preventing diabetes (preferably type II diabetes), diabetes complications (e.g., diabetic nephropathy, diabetic heart disease), and lowering blood glucose or improving glucose tolerance.

In another aspect, the invention also relates to a method for preventing or treating diabetes (e.g., types I and II diabetes), diabetic complications (e.g., diabetic vasculopathy, diabetic neuropathy, diabetic ophthalmopathy, diabetic nephropathy, diabetic heart disease), lowering blood glucose (e.g., fasting blood glucose and postprandial blood glucose), or increasing glucose tolerance, by administering the above GLP-1(7-37) analogue or a derivative thereof to a subject. In another aspect, the present invention also relates to use of the above GLP-1(7-37) analogue or a derivative thereof in the preparation of a medicament for preventing or treating diabetes (e.g., types I and II diabetes), diabetic complications (e.g., diabetic vasculopathy, diabetic neuropathy, diabetic ophthalmopathy, diabetic nephropathy, diabetic heart disease), lowering blood glucose (e.g., fasting blood glucose and postprandial blood glucose), or increasing glucose tolerance.

In another aspect, the present invention relates to a pharmaceutical composition, a preparation, or a kit comprising the above GLP-1(7-37) analogue.

The present invention also relates to a pharmaceutical composition, a preparation or a kit comprising a derivative of the above GLP-1(7-37) analogue.

In addition to comprising the active ingredient GLP-1(7-37) analogue, or a derivative or a salt thereof, the pharmaceutical composition according to the present invention also comprises a pharmaceutically acceptable excipient. Those skilled in the art are familiar with pharmaceutically acceptable excipients, such as non-toxic fillers, stabilizers, diluents, carriers, solvents or other formulation excipients. For example, diluents, excipients, such as microcrystalline cellulose, mannitol, etc.; fillers, such as starch, sucrose, etc.; binders, such as starch, cellulose derivatives, alginate, gelatin, and/or polyvinyl pyrrolidone; disintegrants, such as calcium carbonate and/or sodium bicarbonate; absorption enhancers, such as quaternary ammonium compounds; surfactants, such as cetyl alcohol; carriers, solvents, such as water, physiological saline, kaolin, bentonite, etc.; lubricants, such as talc, calcium/magnesium stearate, polyethylene glycol, etc. In addition, the pharmaceutical composition of the present invention is preferably an injection.

The present invention also relates to a method for reducing islet β-cell apoptosis, enhancing islet β-cell function, increasing islet β-cell number, and/or restoring islet β-cell glucose sensitivity, including: administering effective amount of the above analogue, derivative, or medicament, pharmaceutical composition to a subject in need.

The present invention also relates to use of the above analogue, derivative, or medicament, pharmaceutical composition in the preparation of a medicament for reducing islet β-cell apoptosis, enhancing islet β-cell function, increasing islet β-cell number, and/or restoring islet β-cell glucose sensitivity.

In the present invention, GLP-1(7-37) polypeptide, GLP-1(7-37) polypeptide analogue, and GLP-1(7-37) analogue may be used interchangeably, which refers to a polypeptide containing the amino acid sequence of: $HX_8EGTFTSDVSSX_{19}LEEX_{23}AARX_{27}FIX_{30}WLVX_{34}GX_{36}X_{37}$ (SEQ ID NO: 39), wherein $X_8$ is selected from V, T, I, L, G, or S; $X_{19}$ is Y or K; $X_{23}$ is Q or K; $X_{27}$ is E or K; $X_{30}$ is A or K; $X_{34}$ is R or K; $X_{36}$ is R or K; $X_{37}$ is G or K. The GLP-1(7-37) polypeptide analogue is linked to an extension portion to form a derivative of the GLP-1(7-37) polypeptide analogue. In particular, the invention relates to an acylated derivative of the GLP-1(7-37) analogue. Compared with Semaglutide as the currently recognized best medicament, the acylated derivative not only has a significant therapeutic effect, but also exhibits an increased duration of in vivo activity by about 1 times, which means that in humans the dosing frequency of at least weekly intervals, even biweekly intervals, or longer intervals can be achieved.

The derivative of the GLP-1(7-37) analogue, the acylated derivative of the GLP-1(7-37) analogue, the GLP-1(7-37) derivative, and the GLP-1 derivative of the present invention may be used interchangeably.

In another aspect, the present invention also relates to a method for preparing the above derivative or a pharmaceutically acceptable salt thereof, comprising:

(1) mixing a solution in which the above GLP-1 analogue is dissolved with a solution in which the extension portion (e.g., fatty acid) is dissolved;

(2) adjusting the pH to 4-5 to quench the reaction, standing until a precipitate is generated, and then collecting the precipitate; and (3) adding TFA to the precipitate, and adjusting the pH to 7.5-8.5 to quench the reaction.

In a preferred embodiment, the above method includes adding triethylamine to a solution of the GLP-1 analogue.

In a preferred embodiment, the above extension portion (e.g., fatty acid) is dissolved in an acetonitrile solution.

An exemplary preparation method of the present invention includes:

(1) providing a solution of the GLP-1(7-37) analogue, and adjusting the pH to 9-12;

(2) then adding triethylamine to the solution obtained in step (1);

(3) weighing the fatty acid of the following structure and taking no less than 2 times the amount (molar ratio) of the GLP-1 analogue, preferably no less than 3 times the amount of the GLP-1 analogue, and dissolving it in acetonitrile;

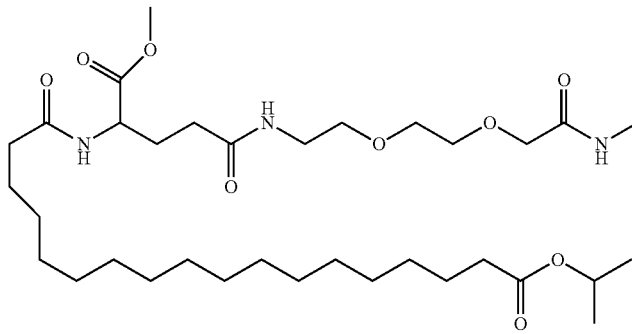
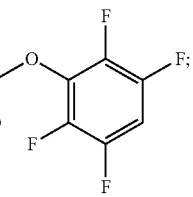

(4) mixing the GLP-1 analogue solution obtained in step (2) with the fatty acid solution obtained in step (3), and standing at a low temperature, e.g., for one hour;

(5) adjusting the pH to 4-5 to quench the reaction, standing at low temperature for acid precipitation, and then collecting the precipitation;

(6) adding TFA to the acid precipitation sample obtained in step (5) to a final polypeptide concentration of 5-15 mg/ml, standing for 0.5-2 hours, and dropping an alkaline solution such as NaOH into the reaction solution, adjusting the pH to 7.5-8.5 to quench reaction;

(7) isolating and purifying the resulting product.

The present invention relates to a preparation of the pharmaceutical composition comprising a derivative of the GLP-1(7-37) analogue or a pharmaceutically acceptable salt thereof. In some embodiments, a derivative of the GLP-1 (7-37) analogue or a pharmaceutically acceptable salt thereof according to the invention is present at a concentration of 0.1-25 mg/ml, preferably is present at a concentration of 0.1-10.0 mg/ml. In a preferred embodiment, the pharmaceutical composition has a pH of 3.0-9.0. In a preferred embodiment, the pharmaceutical composition may further include a buffer system, a preservative, a surface tension agent, a chelating agent, a stabilizer, and a surfactant. In some embodiments, the medicament or preparation described herein is an aqueous medicament or preparation, for example, it may generally be a solution or suspension. In a specific embodiment of the present invention, the medicament or preparation is a stable aqueous solution. In other specific embodiments of the present invention, the medicament or preparation is a lyophilized preparation, and a solvent and/or diluent is added to it before use.

The present invention also relates to a medical box or a kit comprising the above pharmaceutical composition, preparation, or medicament. In addition to the above medicament or preparation, the medical box or kit also comprises other medicament, pharmaceutical compound or composition that may be used in combination with the pharmaceutical composition, preparation, or medicament, for example, the other medicament, pharmaceutical compound or composition may be selected from anti-diabetic medicaments, medicaments for treating and/or preventing complications caused by or related to diabetes. Examples of these medicaments include: insulin, sulfonylurea, biguanides, megliginides, glucosidase inhibitors, glucagon antagonists, inhibitors of liver enzymes involved in stimulating gluconeogenesis and/or glycogenolysis, glucose uptake modulators, NPY antagonists, PYY agonists, PYY2 agonists, PYY4 agonists, TNF agonists, corticotropin releasing factor agonists, 5HT, cerulein agonists, ganglion peptide antagonists, growth hormone, thyrotropin releasing hormone agonists, TRβ agonists; histamine H3 antagonists, lipase/amylase inhibitors, gastric inhibitory polypeptide agonists or antagonists, gastrin and gastrin analogues, etc. In some embodiments, the pharmaceutical composition, preparation, medicament and other medicaments, pharmaceutical compounds or compositions of the present invention are placed in separate containers.

The present invention also relates to a method for preventing or treating diabetes (e.g., types I and II diabetes), diabetic complications (e.g., diabetic vasculopathy, diabetic neuropathy, diabetic ophthalmopathy, diabetic nephropathy, diabetic heart disease), lowering blood glucose (e.g., fasting blood glucose and postprandial blood glucose), comprising: administrating the above analogue, derivative or medicament, pharmaceutical composition to a subject in need, wherein the analogue, derivative or medicament, pharmaceutical composition and other medicament, pharmaceutical compound or composition are used in combination, for example, the other medicament, pharmaceutical compound or composition may be selected from anti-diabetic medicaments, medicaments for treating and/or preventing complications caused by or related to diabetes. Examples of these medicaments include: insulin, sulfonylurea, biguanides, megliginides, glucosidase inhibitors, glucagon antagonists, inhibitors of liver enzymes involved in stimulating gluconeogenesis and/or glycogenolysis, glucose uptake modulators; CART agonists, NPY antagonists, PYY agonists, PYY2 agonists, PYY4 agonists, TNF agonists, corticotropin releasing factor agonists, 5HT, cerulein agonists, ganglion peptide antagonists, growth hormone, thyrotropin releasing hormone agonists, TRO agonists; histamine H3 antagonists, lipase/amylase inhibitors, gastric inhibitory polypeptide agonists or antagonists, gastrin and gastrin analogues, etc. In preferred embodiments, the diabetes is type II diabetes or diabetic nephropathy.

"Diabetic complication" in the present invention refers to a disease of damage or dysfunction of other organs or tissues of the body caused by poor blood glucose control during diabetes, including damage or dysfunction of liver, kidney, heart, retina, nervous system, etc. The complications of diabetes may be divided into five aspects: 1. cardiovascular disease: including microvascular lesions on the heart and large vessels, cardiomyopathy, cardiac autonomic neuropathy, which is the leading cause of death in patients with diabetes; 2. cerebrovascular disease: referring to intracranial macrovascular and microvascular disease caused by diabetes, mainly manifesting as cerebral arteriosclerosis, ischemic cerebrovascular disease, cerebral hemorrhage, cerebral atrophy, etc.; 3. renal vascular disease: mainly manifesting as diabetic nephropathy, which is one of the most important comorbidities of diabetic patients; 4. lower extremity arterial disease: mainly manifesting as diabetic foot; 5. fundus microvascular disease: mainly manifesting as diabetic retinopathy.

The present invention is further illustrated by the following examples. However, the described examples should not be construed as limiting the scope of protection of the patent. The features (individually and in any combination) disclosed in the foregoing description and the following examples may be materials used to realize the present invention in basically different forms, and they may be combined arbitrarily. In addition, the present invention cites public documents, and these documents are intended to clearly describe the present invention. Their entire contents are incorporated herein by reference, as if their full texts have been repeated in this document.

DETAILED DESCRIPTION OF THE INVENTION

Examples

Figure 1:
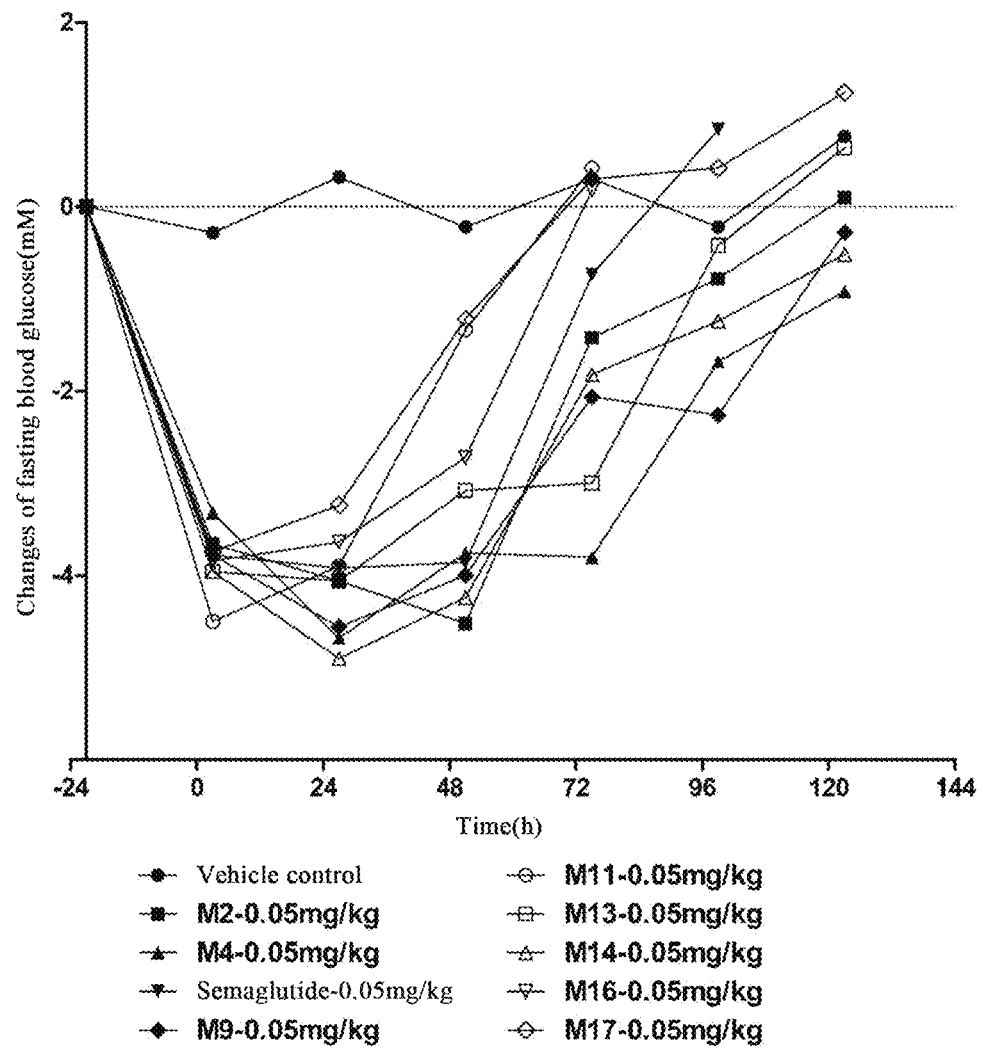
FIG. 1 shows the glucose-lowering effects of different acylated GLP-1 derivative molecules on type II diabetic db/db mice.

Hereinafter, the invention will be described through specific examples. Unless otherwise specified, it may be implemented according to the methods listed in the experimental manuals such as "Molecular Cloning: A Laboratory Manual" and "Cells: A Laboratory Manual" familiar to those skilled in the art, as well as CFDA's experimental guidelines. Among them, the reagent raw materials used are all commercially available products, which may be purchased through public channels.

Example 1: Construction of the Expression Plasmids of GLP-1 Analogues

Construction of DNA of $Val^8Glu^{22}Lys^{23}Arg^{26, 34}$-GLP-1(7-37)

The 6-His tag, SUMO tag, and $Val^8Glu^{22}Lys^{23}Arg^{26,34}$-GLP-1(7-37) encoding gene sequence (SEQ ID NO:7) are fused successively in series, and the gene fragment (SEQ ID NO:18) is obtained by chemical synthesis. Through the BamHI and XhoI sites, the above fragment is inserted into the prokaryotic expression plasmid pET-24(+) and verified by sequencing. The resulting expression plasmid for transformation assay is named pET-24(+)-His-SUMO-$Val^8Glu^{22}Lys^{23}Arg^{26, 34}$-GLP-1(7-37).

According to the above method, the corresponding expression plasmids of the following peptides are successively constructed:

(the encoding gene is SEQ ID NO: 3)
$Val^8Glu^{22}Lys^{26}Arg^{34}$-GLP-1(7-37), (the encoding gene is SEQ ID NO: 11)
$Val^8Glu^{22}Lys^{30}Arg^{26, 34}$-GLP-1(7-37), (the encoding gene is SEQ ID NO: 5)
$Val^8Glu^{22}Lys^{19}Arg^{26, 34}$-GLP-1(7-37), (the encoding gene is SEQ ID NO: 9)
$Val^8Glu^{22}Lys^{27}Arg^{26, 34}$-GLP-1(7-37), (the encoding gene is SEQ ID NO: 13)
$Val^8Glu^{22}Lys^{34}Arg^{26}$-GLP-1(7-37), (the encoding gene is SEQ ID NO: 15)
$Val^8Glu^{22}Arg^{26, 34}Lys^{36}$-GLP-1(7-37), (the encoding gene is SEQ ID NO: 17)
$Val^8Glu^{22}Arg^{26, 34}Lys^{37}$-GLP-1(7-37), (the encoding gene is SEQ ID NO: 20)
$Thr^8Glu^{22}Lys^{23}Arg^{26, 34}$-GLP-1(7-37), (the encoding gene is SEQ ID NO: 22)
$Ile^8Glu^{22}Lys^{23}Arg^{26, 34}$-GLP-1(7-37), (the encoding gene is SEQ ID NO: 24)
$Leu^8Glu^{22}Lys^{23}Arg^{26, 34}$-GLP-1(7-37), (the encoding gene is SEQ ID NO: 26)
$Gly^8Glu^{22}Lys^{23}Arg^{26, 34}$-GLP-1(7-37), (the encoding Gene is SEQ ID NO: 28)
$Ser^8Glu^{22}Lys^{23}Arg^{26, 34}$-GLP-1(7-37), (the encoding gene is SEQ ID NO: 30)
$Thr^8Glu^{22}Lys^{30}Arg^{26, 34}$-GLP-1(7-37), (the encoding gene is SEQ ID NO: 32)
$Ile^8Glu^{22}Lys^{30}Arg^{26, 34}$-GLP-1(7-37), (the encoding gene is SEQ ID NO: 34)
$Leu^8Glu^{22}Lys^{30}Arg^{26, 34}$-GLP-1(7-37), (the encoding gene is SEQ ID NO: 36)
$Gly^8Glu^{22}Lys^{30}Arg^{26, 34}$-GLP-1(7-37), (the encoding gene is SEQ ID NO: 38)
$Ser^8Glu^{22}Lys^{30}Arg^{26, 34}$-GLP-1(7-37).

Example 2: Expression of the Fusion Proteins

The DNA construct described in Example 1 is transformed into BL21 host cells (TrabsGenBiotech, catalog #CD601) for producing the target protein of the present invention. 50 μl of BL21 competent cells are put in an ice bath to melt, then adding the DNA of interest and gently shaking gently, and placing in the ice bath for 30 min. Then heat shock in water bath at 42° C. for 30 seconds, followed by quickly transferring the centrifuge tube to ice bath for 2 min, and do not shake the centrifuge tube during this process. 500 μl of sterile LB medium (without antibiotics) is added to the centrifuge tube, then mixing and culturing at 37° C., 180 rpm for 1 hour to recover the bacteria. 200 μl of transformed competent cells are pipetted and added onto LB agar medium plate containing kanamycin resistance, spreading the cells evenly; placing the plate at 37° C. until the liquid is absorbed, then inverting the plate and incubating at 37° C. overnight. The next day, the monoclonal colonies in the transformation dish is picked by using inoculation ring to inoculate in 15 ml of sterile LB medium (containing antibiotics), then culturing at 30° C. overnight.

Example 3: Fermentation of the Recombinant GLP-1 Analogues

50 μl of bacterial suspension (GLP-1 expressing bacterial suspension) is added to 50 ml of LB medium, adding 50 μl of kanamycin at the same time, mixing and putting in 30° C. constant temperature shaker, then inoculating overnight. 10 ml of the bacterial suspension inoculated overnight is added to 1000 ml of LB medium, adding 1000 μl of kanamycin at the same time; then shaking and placing it in a 37° C. shaker at 200 rpm. After inoculation for 4 hours, IPTG with a final concentration of 0.1 mol/L is added into the medium, then shaking and placing it in 30° C. shaker at 180 rpm to induce expression overnight. The bacterial suspension expressed overnight is centrifuged at 13000 g for 60 min. The bacteria yield is about 4 g bacteria/L fermentation broth, and the expression of the protein of interest determined by SDS-PAGE is about up to 40%.

Example 4: Purification of the Recombinant GLP-1 Analogues 100 g of cell slurry is weighed and re-suspended in 500 ml of 50 mM Tris-HCl, pH 8.0, 50 mM NaCl, then sonicating in an ultrasonic cell mill for 30 min to break up the cells. The homogenate is centrifuged at 13000 g for 60 min at 4° C. After centrifugation the supernatant is collected as Ni column chromatography sample.

The obtained supernatant is concentrated by Chelating Sepharose FF equilibrated with 50 mM Tris-HCl, pH 8.0, 500 mM NaCl, 10 mM imidazole (equilibrium liquid 1) in advance; after rinsing with the equilibrium liquid 1, it is eluted with 50 mM Tris-HCl, pH 8.0, 50 mM NaCl, and 0.3 M imidazole (eluent). According to SDS-PAGE analysis, the purity of the intermediate product of GLP-1 produced by the above purification process is higher than 70%.

Excising the Sumo tag sequence by using ULP enzyme: adding 20 mM PB, pH7.4 buffer to the intermediate product to make a three-fold dilution, adding ULP enzyme to mix and digest overnight at the condition of 4° C. at a 1:150 ratio of ULP enzyme:the intermediate product. The digestion rate is nearly 100% according to SDS-PAGE analysis.

Purification of GLP-1 analogue: the product obtained after digestion is concentrated by using Tosoh Butyl 550C medium equilibrated with 20 mM $Na_2HPO_4$, 0.7M NaCl (equilibrium liquid 2) in advance, after rinsing with the equilibrium liquid 2, it is eluted with 20% ethanol, and the purity is about 90% according to SDS-PAGE analysis.

0.2M $Na_2HPO_4$ is added to the eluted sample to make a final concentration of 20 mM $Na_2HPO_4$, then adjusting the pH to 4.8-5.0 with 1M citric acid for acid precipitation at 4° C. overnight. The yield is over 90% according to SDS-PAGE assay. Centrifuging at 13000 g for 30 min at 4° C., then the precipitate is collected and stored at −20° C.

Example 5: Preparation of the Derivatives of GLP-1 Analogues

Preparation of the derivative of GLP-1 analogue as shown below, N-$\varepsilon^{23}$-[2-(2-[2-(2-[2-(2-[4-(17-carboxyheptadecanoylamino)-4(s)-carboxybutyrylamino]ethoxy)ethoxy]acetylamino)ethoxy]ethoxy)acetyl](Val$^8$Glu$^{22}$Lys$^{23}$Arg$^{26,34}$-GLP-1(7-37)) peptide (abbreviated as M2)

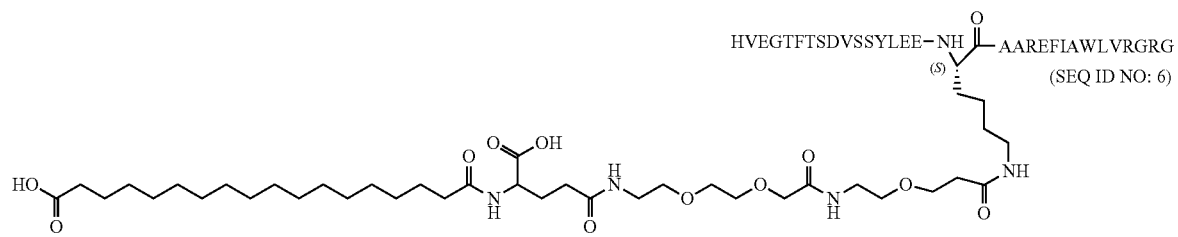

1. Fatty acid modification: water is added to the precipitate of Val$^8$Gu$^{22}$Lys$^{23}$Arg$^{26,\ 34}$-GLP-1(7-37) prepared and collected in the above example to prepare 4-6 mg/ml solution, then adding 1M sodium hydroxide to adjust the pH to 11.0-11.5, shaking to make the protein completely dissolved, and the concentration of the peptide is quantified by HPLC. Fatty acid powder is weighed and dissolved in acetonitrile at a 1:4 molar ratio of the peptide to fatty acid (the structure is as follows). Two thousandths of triethylamine is added to this polypeptide solution, mixing with the fatty acid solution, and letting the mixture stand at 4° C. for one hour.

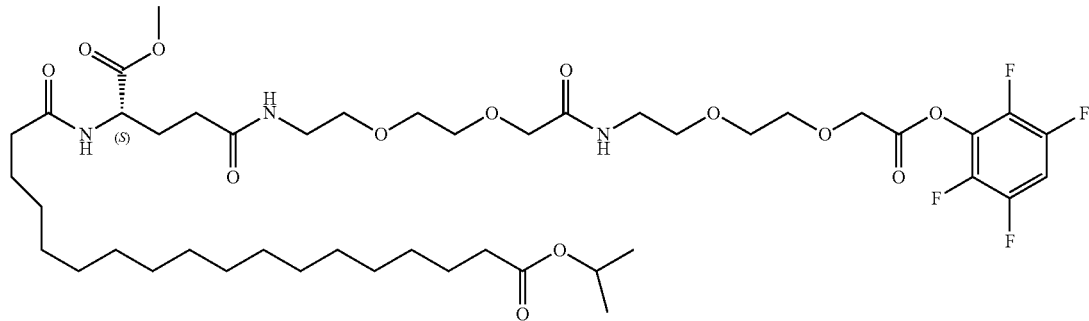

The sample is diluted 5 times with water, then adjusting to pH 4.8 with 1M citric acid (or 10% acetic acid) to quench the reaction, standing at 4° C. for acid precipitation for 10 min, centrifuging at 13000 g after acid precipitation and centrifuging at 4° C. for 30 min, and then the precipitate is stored at −80° C.

2. Deprotection of fatty acid and purification: TFA is added to the acid precipitation sample to a final peptide concentration of about 10 mg/ml, then shaking to dissolve the precipitate, letting it stand at room temperature for deprotection for 30 min, and dropping 4M NaOH into the reaction solution to adjust the pH to 7.5-8.5 to quench the reaction.

By using a preparative HPLC (Shimadzu LC-8A), the reaction liquid after quenching is pumped into UniSil 10-120 C18 (purchased from Suzhou Nanomicro Technology Co., Ltd.) equilibrated with 10 mM ammonium acetate, 20% ethanol (equilibrium liquid 3) in advance for concentration. After rinsing with the equilibrium liquid 3, a gradient of 0-100% eluent (10 mM ammonium acetate, 80% ethanol) is used for elution. The elution peak is collected, and the purity is about 90% according to RP-HPLC analysis.

The elution peak is diluted 3 times with water, then adjusting the pH of acid precipitation to 4.80, and acid precipitation is performed at 4° C. for 30 min. After centrifugation, PBST buffer (pH7.0) is added to the pellet to reconstitute it, then freezing and storing at −80° C.

The following peptides are prepared successively according to the above method, N-$\varepsilon^{26}$-[2-(2-[2-(2-[2-(2[4-(17-carboxyheptadecanoylamino)-4(s)-carboxybutyrylamino]ethoxy)ethoxy]acetylamino)ethoxy]ethoxy)acetyl] Val$^8$Gu$^{22}$Lys$^{26}$Arg$^{34}$-GLP-1(7-37) peptide (M0), N-$\varepsilon^{30}$-[2-(2-[2-(2-[2-(2-[4-(17-carboxyheptadecanoylamino)-4(s)-carboxybutyrylamino]ethoxy)ethoxy]acetylamino)ethoxy]ethoxy)acetyl])(Val$^8$Glu$^{22}$Lys$^{30}$Arg$^{26,34}$-GLP-1(7-37)) peptide (M4), N-$\varepsilon^{19}$-[2-(2-[2-(2-[2-(2-[4-(17-carboxyheptadecanoylamino)-4(s)-carboxybutyrylamino]ethoxy)ethoxy]acetylamino)ethoxy]ethoxy)acetyl](Val$^8$Lys$^{19}$Gu$^{22}$Arg$^{26,34}$-GLP-1(7-37)) peptide (M1), N-$\varepsilon^{27}$-[2-(2-[2-(2-[2-(2-[4-(17-carboxyheptadecanoylamino)-4(s)-carboxybutyrylamino]ethoxy)ethoxy]acetylamino)ethoxy]ethoxy)acetyl](Val$^8$Glu$^{22}$Lys$^{27}$Arg$^{26,34}$-GLP-1(7-37)) peptide (M3), N-$\varepsilon^{34}$-[2-(2-[2-(2-[2-(2-[4-(17-carboxyheptadecanoylamino)-4(s)-carboxybutyrylamino]ethoxy)ethoxy]acetylamino)ethoxy]ethoxy)acetyl](Val$^8$Gu$^{22}$Arg$^{26}$Lys$^{34}$-GLP-1(7-37)) peptide (M5), N-$\varepsilon^{36}$-[2-(2-[2-(2-[2-(2-[4-(17-carboxyheptadecanoylamino)-4(s)-carboxybutyrylamino]ethoxy)ethoxy]acetylamino)ethoxy]ethoxy)acetyl] (Val$^8$Glu$^{22}$Arg$^{26,34}$Lys$^{36}$-GLP-1(7-37)) peptide (M6), N-$\varepsilon^{37}$-[2-(2-[2-(2-[2-(2-[4-(17-carboxyheptadecanoylamino)-4(s)-carboxybutyrylamino]ethoxy)ethoxy]acetylamino)ethoxy]ethoxy)acetyl](Val$^8$Glu$^{22}$Arg$^{26,34}$Lys$^{37}$-GLP-1(7-37)) peptide (M7); N-$\varepsilon^{23}$-[2-(2-[2-(2-[2-(2-[4-(17-carboxyheptadecanoylamino)-4(s)-carboxybutyrylamino]ethoxy)ethoxy]acetylamino)ethoxy]ethoxy)acetyl] (Thr$^8$Gu$^{22}$Lys$^{23}$Arg$^{26,34}$-GLP-1(7-37)) peptide (M8), N-$\varepsilon^{23}$-[2-(2-[2-(2-[2-(2-[4-(17-carboxyheptadecanoylamino)-4(s)-carboxybutyrylamino]ethoxy)ethoxy]acetylamino)ethoxy]ethoxy)acetyl](Ile$^8$Glu$^{22}$Lys$^{23}$Arg$^{26,34}$-GLP-1(7-37)) peptide (M9), N-$\varepsilon^{23}$-(2-(2-[2-(2-[2-(2-[4-(17-carboxyheptadecanoylamino)-4(s)-carboxybutyrylamino]ethoxy)ethoxy]acetylamino)ethoxy]ethoxy)acetyl] (Leu$^8$Glu$^{22}$Lys$^{23}$Arg$^{26,34}$-GLP-1(7-37)) peptide (M10), N-$\varepsilon^{23}$-[2-(2-[2-(2-[2-(2-[4-(17-carboxyheptadecanoylamino)-4(s)-carboxybutyrylamino]ethoxy)ethoxy]acetylamino)ethoxy]ethoxy)acetyl](Gly$^8$Glu$^{22}$Lys$^{23}$Arg$^{26,34}$-GLP-1(7-37)) peptide (M11), N-$\varepsilon^{23}$-[2-(2-[2-(2-[2-(2-[4-(17-carboxyheptadecanoylamino)-4(s)-carboxybutyrylamino]ethoxy)ethoxy]acetylamino)ethoxy]ethoxy)acetyl)](Ser$^8$Gu$^{22}$Lys$^{23}$Arg$^{26,34}$-GLP-1(7-37)) peptide (M12); N-$\varepsilon^{30}$-[2-(2-[2-(2-[2-(2-[4-(17-carboxyheptadecanoylamino)-4(s)-carboxylbutyrylamino]ethoxy)ethoxy]acetylamino)ethoxy]ethoxy)acetyl]) (Thr$^8$Gu$^{22}$Lys$^{30}$Arg$^{26,34}$-GLP-1(7-37)) peptide (M13), N-$\varepsilon^{30}$-[2-(2-[2-(2-[2-(2-[4-(17-carboxyheptadecanoylamino)-4(s)-carboxybutyrylamino]ethoxy)ethoxy]acetylamino)ethoxy]ethoxy)acetyl](Ile$^8$Glu$^{22}$Lys$^{30}$Arg$^{26,34}$-GLP-1(7-37)) peptide (M14), N-$\varepsilon^{30}$-[2-(2-[2-(2-[2-(2-[4-(17-carboxyheptadecanoylamino)-4(s)-carboxybutyrylamino]ethoxy)ethoxy]acetylamino)ethoxy]ethoxy)acetyl](Leu$^8$Glu$^{22}$Lys$^{30}$Arg$^{26,34}$-GLP-1(7-37)) peptide (M5), N-$\varepsilon^{30}$-[2-(2-[2-(2-[2-(2-[4-(17-carboxyheptadecanoylamino)-4(s)-carboxybutyrylamino]ethoxy)ethoxy]acetylamino)ethoxy)acetyl](Gly$^8$Glu$^{22}$Lys$^{30}$Arg$^{26,34}$-GLP-1(7-37)) peptide (M6), N-$\varepsilon^{30}$-[2-(2-[2-(2-[2-(2-[4-(17-carboxyheptadecanoylamino)-4 (s)-carboxybutyryl amino]ethoxy)ethoxy]acetylamino)ethoxy]ethoxy)acetyl](Ser$^8$Glu$^{22}$Lys$^{30}$Arg$^{26,34}$-GLP-1(7-37)) peptide (M7).

TABLE 1

Comparison table of GLP-1(7-37) analogues and their corresponding derivatives

| Abbreviations of the derivatives | Abbreviations of the GLP-1 analogues | Amino acid sequences of the GLP-1 analogues |
|---|---|---|
|  | GLP-1(7-37) | HAEGTFTSDVSSYLEGQAAKEFIA WLVKGRG (SEQ ID NO: 1) |
| Semaglutide (Aib) | Aib$^8$Lys$^{26}$Arg$^{34}$-GLP-1 (7-37) | H-Aib-EGTFTSDVSSYLEGQAAKE FIAWLVRGRG (SEQ ID NO: 40) |
| M0 | Val$^8$Glu$^{22}$Lys$^{26}$Arg$^{34}$-GLP-1 (7-37) | HVEGTFTSDVSSYLEEQAAKEFIA WLVRGRG (SEQ ID NO: 2) |
| M1 | Val$^8$Lys$^{19}$Glu$^{22}$Arg$^{26, 34}$-GLP-1 (7-37) | HVEGTFTSDVSSKLEEQAAREFIA WLVRGRG (SEQ ID NO: 4) |
| M2 | Val$^8$Glu$^{22}$Lys$^{23}$Arg$^{26, 34}$-GLP-1 (7-37) | HVEGTFTSDVSSYLEEKAAREFIA WLVRGRG (SEQ ID NO: 6) |
| M3 | Val$^8$Glu$^{22}$Lys$^{27}$Arg$^{26, 34}$-GLP-1 (7-37) | HVEGTFTSDVSSYLEEQAARKFIA WLVRGRG (SEQ ID NO: 8) |
| M4 | Val$^8$Glu$^{22}$Lys$^{30}$Arg$^{26, 34}$-GLP-1 (7-37) | HVEGTFTSDVSSYLEEQAAREFIK WLVRGRG (SEQ ID NO: 10) |
| M5 | Val$^8$Glu$^{22}$Arg$^{26}$Lys$^{34}$-GLP-1 (7-37) | HVEGTFTSDVSSYLEEQAAREFIA WLVKGRG (SEQ ID NO: 12) |
| M6 | Val$^8$Glu$^{22}$Arg$^{26, 34}$Lys$^{36}$-GLP-1(7-37) | HVEGTFTSDVSSYLEEQAAREFIA WLVRGKG (SEQ ID NO: 14) |
| M7 | Val$^8$Glu22Arg$^{26, 34}$Lys$^{37}$-GLP-1(7-37) | HVEGTFTSDVSSYLEEQAAREFIA WLVRGRK (SEQ ID NO: 16) |
| M8 | Thr$^8$Glu$^{22}$Lys$^{23}$Arg$^{26, 34}$-GLP-1(7-37) | HTEGTFTSDVSSYLEEKAAREFIA WLVRGRG (SEQ ID NO: 19) |
| M9 | Ile$^8$Glu$^{22}$Lys$^{23}$Arg$^{26, 34}$-GLP-1(7-37) | HIEGTFTSDVSSYLEEKAAREFIA WLVRGRG (SEQ ID NO: 21) |
| M10 | Leu$^8$Glu$^{22}$Lys$^{23}$Arg$^{26, 34}$-GLP-1(7-37) | HLEGTFTSDVSSYLEEKAAREFIA WLVRGRG (SEQ ID NO: 23) |
| M11 | Gly$^8$Glu$^{22}$Lys$^{23}$Arg$^{26, 34}$-GLP-1(7-37) | HGEGTFTSDVSSYLEEKAAREFIA WLVRGRG (SEQ ID NO: 25) |
| M12 | Ser$^8$Glu$^{22}$Lys$^{23}$Arg$^{26, 34}$-GLP-1(7-37) | HSEGTFTSDVSSYLEEKAAREFIA WLVRGRG (SEQ ID NO: 27) |
| M13 | Thr$^8$Glu$^{22}$Lys$^{30}$Arg$^{26, 34}$-GLP-1(7-37) | HTEGTFTSDVSSYLEEQAAREFIK WLVRGRG (SEQ ID NO: 29) |
| M14 | Ile$^8$Glu$^{22}$Lys$^{30}$Arg$^{26, 34}$-GLP-1(7-37) | HIEGTFTSDVSSYLEEQAAREFIK WLVRGRG (SEQ ID NO: 31) |
| M15 | Leu$^8$Glu$^{22}$Lys$^{30}$Arg$^{26, 34}$-GLP-1(7-37) | HLEGTFTSDVSSYLEEQAAREFIK WLVRGRG (SEQ ID NO: 33) |
| M16 | Gly$^8$Glu$^{22}$Lys$^{30}$Arg$^{26, 34}$-GLP-1(7-37) | HGEGTFTSDVSSYLEEQAAREFIK WLVRGRG (SEQ ID NO: 35) |
| M17 | Ser$^8$Glu$^{22}$Lys$^{30}$Arg$^{26, 34}$-GLP-1(7-37) | HSEGTFTSDVSSYLEEQAAREFIK WLVRGRG (SEQ ID NO: 37) |

Example 6: In Vitro Activity Determination of Derivatives of GLP-1 Analogues in RIN-m5F Cells RIN-m5F cells with good culturing status are selected. Cells are then collected, counted, and prepared into a cell suspension of $1 \times 10^5$ cells/ml with RPMI1640 basal medium. The cell suspension is inoculated in a 96-well cell culture plate, 100 μl per well, then incubating overnight at 37° C. and 5% $CO_2$. The in vitro activity of the derivatives of GLP-1 analogs is measured by using cAMP assay kit (Promega): preparing diluted samples (Aib, M0, M1, M2, M3, M4, M5, M6, and M7) to 300 ng/ml with the assay medium, then performing a 3-fold gradient dilution in 96-well plates, a total of 8 concentrations, and making 2 duplicate wells for each dilution, wherein M0, M1, M2, M3, M4, M5, M6, and M7 are prepared as described above, and Aib is:

N-ε$^{26}$-[2-(2-[2-(2-[2-(2[4-(17-carboxyheptadecanoylamino)-4(s)-carboxybutyrylamino]ethoxy) ethoxy]acetylamino)ethoxy]ethoxy)acetyl][Aib$^8$, Arg$^{34}$]GLP-1-(7-37)

peptide (see CN101133082B, Example 4), the trade name is Semaglutide, and it is prepared according to the method disclosed in patent CN101133082B.

The prepared cell plate is taken out, then discarding the medium, and blotting it dry on the filter paper. The sample solutions are transferred correspondingly into the cell plate, 40 μl/well; treating with the lid open for 15 min at 37° C. and 5% $CO_2$. The cell culture plate is taken out from the incubator, then adding 10 μl of CD solution (cAMP assay kit, Promega) to each well, keeping the cell plate at 22-25° C., and shaking horizontally at 500 rpm for 20 min. 50 μl of KG solution (cAMP assay kit, Promega) is added to each well, then shaking horizontally at 22° C.-25° C., 500 rpm and avoiding light for 10 min. The chemiluminescence value is read by using the Molecular Devices SpectraMax L chemiluminescence apparatus, completing the measurement in 30 min. EC50 of a sample is calculated by using the four-parameter regression in softmax Pro software.

TABLE 2

Results of In vitro Activity Assay

| Samples | Aib | M0 | M1 | M2 | M3 | M4 | M5 | M6 | M7 |
|---|---|---|---|---|---|---|---|---|---|
| EC50 | 2.437 | 10.68 | 5.386 | 1.996 | 5.387 | 2.322 | 3.043 | 7.650 | 3.208 |

The in vitro pharmacodynamics of RIN-m5F cells shows that the in vitro activities of Semaglutide, M2, M4, M5, and M7 are comparable, and generally they are slightly higher than those of M0, M1, M3, and M6.

Example 7: In Vitro Activity Determination of the Derivatives of GLP-1 Analogues in HEK293/CRE-Luc/GLP1R Cells Based on the fact that GLP-1 may bind to the receptor on the cell membrane, the HEK293/CRE-Luc/GLP1R cell line is constructed, the cAMP response elements (CRE) are activated through a series of signal transduction, the expression of downstream luciferase is initiated, and the amount of its expression is positively correlated with the biological activity of GLP-1. After adding the luciferase substrate, the chemiluminescence assay is performed to determine the luminous intensity, thereby determining the biological activity of GLP-1.

Experimental Materials 96-well cell culture plate (white and opaque), DMEM medium (GIBCO), 0.05% TRYPSIN-EDTA (GIBCO), fetal bovine serum (GIBCO), G418, hygromycin B, Bright-Glo™ Luciferase Assay System Kit (Promega), and HEK293/CRE-luc/GLP1R cells.

Experimental Operations (1) Cell preparation: the cells are cultured until they grow vigorously and reach a sufficient quantity, discarding the culture medium in the culture bottle, adding 3 ml of Versene solution and shaking once; then adding 2 ml of 0.05% TRYPSIN-EDTA digestion solution, covering the bottle and standing for 1 minute, and then adding 6 ml of the assay medium to quench the digestion; after centrifugation at 1000r/min for 3 min, the supernatant is discarded, and the cells are resuspended in 5 ml of assay medium and counted on a hemacytometer. The cell density is adjusted to an appropriate range for later use by using DMEM assay medium.

(2) Sample preparation: the derivatives of different GLP-1 analogues in Table 1 are diluted to 20 ng/ml with the assay medium, then gradient diluted into 8 concentrations in 96-well plates, and using the assay medium instead of the sample as the cell blank control. 2 duplicate wells are made for each dilution concentration.

(3) Culturing with addition of the samples: the prepared solutions of the control and test samples are transferred to a 96-well cell culture plate (white board), adding 50 μl of the solution to each well; then adding the prepared cell suspension, adding 50 μl of the suspension to each well; and then incubating for a certain period of time under the conditions of 37° C. and 5% $CO_2$.

(4) Chemiluminescence assay: substrate is added, then taking out the 96-well cell culture plate, adding 100 μl of Bright Glo reagent to each well, and leaving in the dark for 3 min.

(5) Reading: determination is performed with a chemiluminescence microplate reader SpectraMax L, then reading the plate within 30 min, and recording the determined results.

TABLE 3

Experimental results of in vitro activity of HEK293/CRE-Luc/GLP1R cells

| Experimental plate 1 | | Experimental plate 2 | | Experimental plate 3 | |
|---|---|---|---|---|---|
| Samples | EC50 | Samples | EC50 | Samples | EC50 |
| Semaglutide | 0.14 | Semaglutide | 0.138 | Semaglutide | 0.111 |
| Liraglutide | 0.206 | Liraglutide | 0.211 | Liraglutide | 0.142 |
| M2 | 0.134 | M4 | 0.184 | M4 | 0.137 |
| M9 | 0.177 | M13 | 0.454 | M16 | 0.13 |
| M11 | 0.183 | M14 | 0.232 | M17 | 0.15 |

The pharmacodynamics of HEK293/CRE-Luc/GLP1R cells shows that the in vitro activities of Semaglutide, M2, M4, M9, M11, M14, M16, and M17 are comparable, and generally they are slightly higher than that of M13.

Example 8: Research on Glucose-Lowering Effect of Fatty Acid Modified Derivatives of GLP-1 Analogues in Normal Mice Twenty-eight healthy female CD-1 mice aged 4-6 weeks are selected and divided into 4 groups, and they are injected subcutaneously and respectively with M2, M4, M0 and Semaglutide (Aib) at a dose of 0.15 mg/kg body weight. 20% glucose is intragastrically administered pre-administration, and after intervals of 6h, 1 day, 2 days, 3 days, and 4 days from administration, at a dose of 2 g/kg body weight, and fasting for 6 hours before giving the glucose; then blood is respectively collected from the tip of the tail at 0h, 0.5h, 1h and 2h after giving the glucose and measured for blood glucose value in real time by using Roche blood glucose test paper; and the blood glucose AUC (area under the curve of blood glucose~time) within 0-120 min is calculated, and the blood glucose inhibition rate is obtained (Table 4).

Blood glucose inhibition rate=[(Blood glucose AUC of mice before administration−Blood glucose AUC of mice after administration)/Blood glucose AUC of mice before administration]×100%

TABLE 4

Comparison of the glucose-lowering effects in normal mice

|  |  | 6 h | 30 h | 54 h | 78 h | 102 h |
|---|---|---|---|---|---|---|
| Semaglutide | Inhibition rate | 35.95% | 30.87% | 21.00% | 1.68% |  |
| 0.15 mg/kg | P | 0.0000 | 0.0000 | 0.0010 | 0.7728 |  |
| M2 | Inhibition rate | 34.29% | 29.51% | 27.23% | 21.97% | 10.15% |
| 0.15 mg/kg | P | 0.0000 | 0.0000 | 0.0000 | 0.0002 | 0.0408 |
| M4 | Inhibition rate | 36.11% | 34.19% | 31.51% | 24.82% | 15.00% |
| 0.15 mg/kg | P | 0.0000 | 0.0000 | 0.0000 | 0.0001 | 0.0064 |
| M0 | Inhibition rate | 38.47% | 33.79% | 25.18% | 13.43% | −1.05% |
| 0.15 mg/kg | P | 0.0000 | 0.0000 | 0.0002 | 0.0180 | 0.7909 |

P value: compared with blood glucose before administration

It may be seen from Table 4 that, the glucose-lowing effect of Semaglutide in normal mice lasts about 2 days, and the glucose-lowering effect of M0 in normal mice lasts about 3 days; however, the glucose-lowering effect of M2 and M4 in normal mice are still obvious on day 4, and their duration of sustained glucose-lowering effect in the body is significantly longer than that of Semaglutide or M0, and at various time points after the 3rd day of administration the glucose-lowering effects of both M2 and M4 are also significantly stronger than that of Semaglutide or M0.

Twenty-eight healthy female CD-1 mice aged 4-6 weeks are selected and divided into 4 groups, and they are injected subcutaneously with M4, M5, M7 and M0 at a dose of 0.15 mg/kg body weight. 20% glucose is intragastrically administered pre-administration and after intervals of 6h, 1 day, 2 days, 3 days, and 4 days from administration, at a dose of 2 g/kg body weight, and fasting for 6 hours before intragastrically administering the 20% glucose; and blood is respectively collected from the tip of the tail at 0h, 0.5h, 1h and 2h after giving the glucose, then measuring the blood glucose value in real time by using Roche blood glucose test paper, and the blood glucose AUC (area under the curve of blood glucose-time) within 0-120 min is calculated, the blood glucose inhibition rate (Table 5) is obtained.

Blood glucose inhibition rate=[(Blood glucose AUC of mice before administration−Blood glucose AUC of mice after administration)/Blood glucose AUC of mice before administration]×100%

From the results of Table 4 and Table 5, the glucose-lowering effects of M2 and M4 are better than those of M0 and Semaglutide; and the glucose-lowering effects of M2, M4, M5 and M7 are comparable, and there is no significant difference between them.

Example 9: Research on the Glucose-Lowing Effect by Using ICR Mice

OGTT test of ICR mice: 30 ICR mice aged 4-6 weeks are selected and divided into 6 groups, 5 mice per group, and they are injected subcutaneously with M0, Semaglutide, M2, M4, M5 and M7 respectively at a dose of 0.15 mg/kg body weight by single administration. 20% glucose is intragastrically administered every day according to the time schedule of 4h, 1d, 2d, 3d, 4d, and 5d, at a dose of 2 g/kg body weight, and fasting for 6 hours before administering the glucose; and blood is respectively collected from the tip of the tail at 0h, 0.5h, 1h and 2h after giving the 20% glucose, then measuring the blood glucose value in real time by using Roche blood glucose test paper. Blood is collected from the tip of the tail, the blood glucose value is measured in real time by using Roche blood glucose test paper, and the blood glucose AUC (area under the curve of blood glucose-time) within 0-120 min is calculated, and the blood glucose inhibition rate (Table 6) is obtained.

Blood glucose inhibition rate=[(Blood glucose AUC of mice before administration−Blood glucose AUC of mice after administration)/Blood glucose AUC of mice before administration]×100%

TABLE 5

Comparison of glucose-lowering effects in normal mice

|  |  | 6 h | 30 h | 54 h | 78 h | 102 h |
|---|---|---|---|---|---|---|
| M0 | Inhibition rate | 26.71% | 33.57% | 17.32% | 8.97% | −12.89% |
| 0.15 mg/kg | P | 0.0018 | 0.0004 | 0.0210 | 0.2329 | 0.2792 |
| M4 | Inhibition rate | 26.26% | 32.92% | 22.22% | 24.07% | 16.55% |
| 0.15 mg/kg | P | 0.0045 | 0.0004 | 0.0066 | 0.0049 | 0.0706 |
| M5 | Inhibition rate | 29.59% | 39.47% | 30.11% | 27.07% | 15.38% |
| 0.15 mg/kg | P | 0.0041 | 0.0006 | 0.0046 | 0.0156 | 0.1144 |
| M7 | Inhibition rate | 27.22% | 38.82% | 22.56% | 22.48% | 11.60% |
| 0.15 mg/kg | P | 0.0049 | 0.0006 | 0.0142 | 0.0084 | 0.1389 |

TABLE 6

Comparison of glucose-lowering effects in ICR mice

| Groups | | 0 h | 4 h | 1 d | 2 d | 3 d | 4 d | 5 d |
|---|---|---|---|---|---|---|---|---|
| M0 | G-AUC | 18.0 ± 1.9 | 11.1 ± 1.2 | 11.9 ± 0.7 | 13.5 ± 1.1 | 15.6 ± 1.3 | 18.2 ± 1.1 | / |
| 0.15 mg/kg | Inhibition rate | / | 38.47% | 33.79% | 25.18% | 13.43% | 0.60% | / |
| Semaglutide | G-AUC | 18.3 ± 2.1 | 11.7 ± 1.2 | 12.7 ± 0.7 | 14.5 ± 1.1 | 18.0 ± 1.8 | / | / |
| 0.15 mg/kg | Inhibition rate | / | 35.95% | 30.87% | 21.00% | 1.68% | / | / |
| M2 | G-AUC | 17.8 ± 1.9 | 11.7 ± 0.6 | 12.5 ± 0.6 | 13.0 ± 0.7 | 13.9 ± 0.6 | 16.0 ± 1.0 | 18.3 ± 0.6 |
| 0.15 mg/kg | Inhibition rate | / | 34.29% | 29.51% | 27.23% | 21.97% | 12.61% | 0.08% |
| M4 | G-AUC | 18.0 ± 1.8 | 11.5 ± 1.0 | 11.8 ± 0.9 | 12.3 ± 0.9 | 13.5 ± 0.9 | 15.3 ± 1.1 | 17.3 ± 1.0 |
| 0.15 mg/kg | Inhibition rate | / | 36.11% | 34.19% | 31.51% | 24.82% | 16.39% | 5.68% |
| M5 | G-AUC | 16.3 ± 2.5 | 11.5 ± 1.0 | 9.9 ± 0.7 | 11.4 ± 1.3 | 11.9 ± 2.0 | 13.8 ± 1.9 | 14.4 ± 2.2 |
| 0.15 mg/kg | Inhibition rate | / | 29.59% | 39.47% | 30.11% | 27.07% | 15.38% | 11.66% |
| M7 | G-AUC | 16.3 ± 2.7 | 11.8 ± 1.4 | 10.0 ± 1.6 | 12.6 ± 1.5 | 12.6 ± 0.7 | 14.4 ± 1.1 | 15.2 ± 1.0 |
| 0.15 mg/kg | Inhibition rate | / | 27.22% | 38.82% | 22.56% | 22.48% | 11.60% | 6.76% |

It may be seen from the results in Table 6 that, the glucose level is maintenance constantly: the glucose-lowering effects of M4, M5, M2, and M7 may all be maintained for at least 4 days, which are much better than those of M0 (only maintained for 3 days) and Semaglutide (only maintained for 2 days), and all of which are statistically significant.

Example 10: Glucose-Lowing Pharmacokinetic Test for Type II Diabetic db/db Mice

Fifty 8-9 week-old female db/db mice are evenly divided into 10 groups based on body weight and fasting blood glucose value (FBG) before administration, 5 mice per group; and they are respectively administered with a single subcutaneous injection of vehicle, M2, M4, Semaglutide, M9, M11, M13, M14, M16 and M17 at 10 ml/kg. The dosage is 0.05 mg/kg for each, and the administration time is set as 0h. Fasting blood glucose is measured after fasting for 6-8h every day, and the fasting blood glucose after administration is measured every day until the fasting blood glucose value of each animal of the test group recovers to the value measured before administration. The blood glucose value measured before administration is called the basal blood glucose value, and is set as 0.

Change of the fasting blood glucose (Δ: delta)=Blood glucose value after administration−Basal blood glucose value before administration.

The results are shown in FIG. 1, it may be seen from day 4 and day 5 that the glucose-lowering effects of M9, M13, and M14 are better than that of Semaglutide, and are also not lower than that of M2; however, the glucose-lowering effects of M11, M16 and M17 are lower than that of Semaglutide on day 2.

Example 11: Glucose-Lowing Effect of Different Doses of Semaglutide, M0 and M4 for Type II Diabetic db/db Mice Thirty-five 8-9 week-old female db/db mice are evenly divided into 7 groups based on body weight and blood glucose area under the curve (G-AUC) before administration, 5 mice per group; and they are respectively administered with a single subcutaneous injection of vehicle, M4 (0.15, 0.015 mg/kg), Semaglutide (0.15, 0.015 mg/kg), and M0 (0.15, 0.015 mg/kg) at 10 ml/kg. The administration time is set as 0h, and the fasting blood glucose and OGTT (oral glucose tolerance assay) are determined after fasting for 7-8h every day, then 10% glucose is intragastrically administered at 1 g/kg body weight, and then blood is collected from the tip of the tail to measure the blood glucose in real time at 0, 0.5, 1, and 2h after glucose load. After administration, the blood glucose is measured every day before fasting as random blood glucose, until the fasting blood glucose value of each animal of the test group recovers to the value before administration. All of the basal blood glucose value, random blood glucose value, and the blood glucose area under the curve (G-AUC) value determined before administration are bases for evaluating the efficacy of the medicament, and they are set as 0.

Change of the blood glucose (Δ: delta)=Blood glucose value after administration−Basal blood glucose value before administration.

Change of the blood glucose area under the curve (Δ: delta)=blood glucose area under the curve after administration−blood glucose area under the curve before administration.

Figure 2:
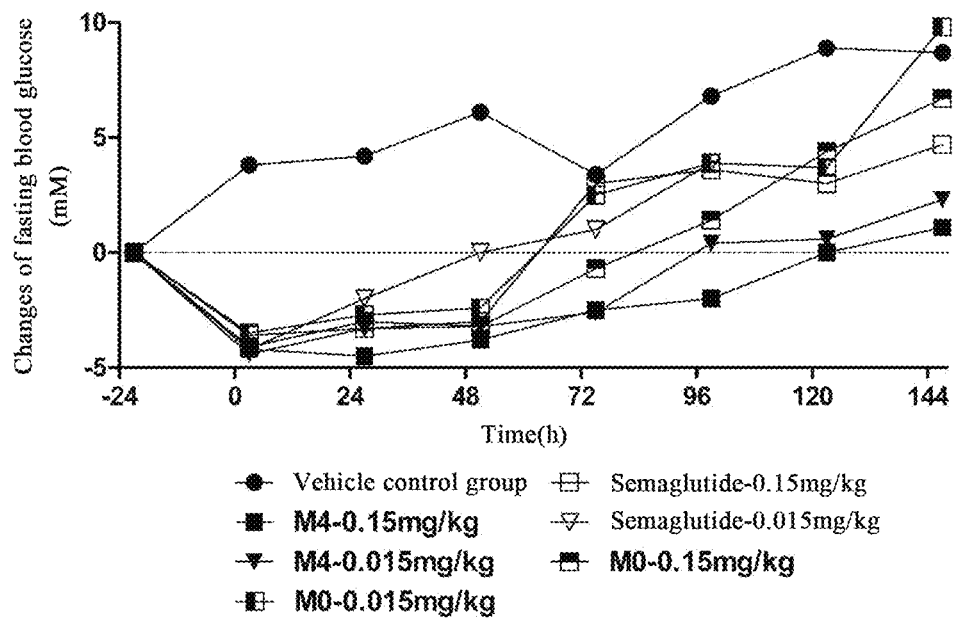
FIG. 2 shows a trend graph of the effects of different doses of M0, M4, and Semaglutide on fasting blood glucose in diabetic mice.
Figure 3:
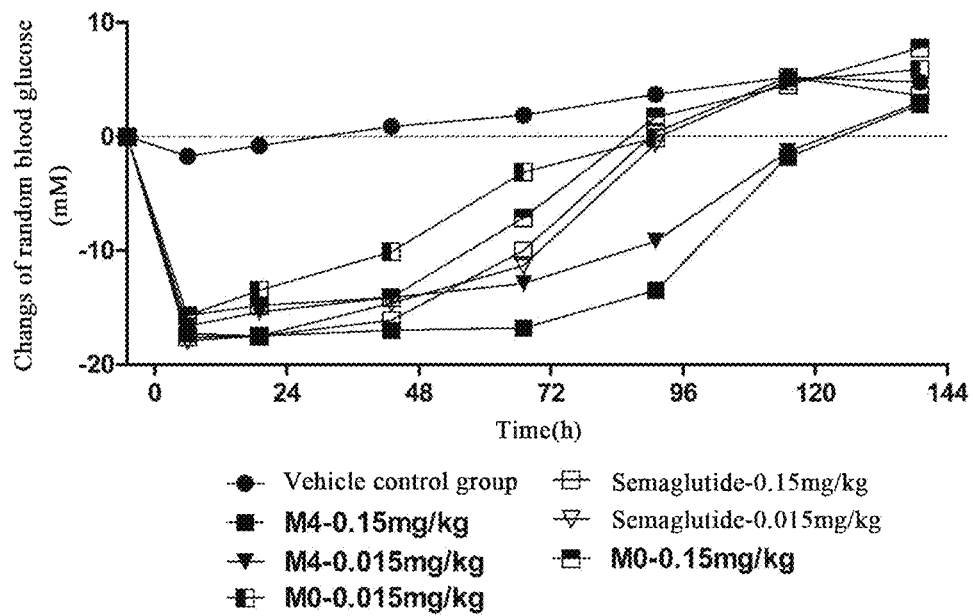
FIG. 3 shows the effects of different doses of M0, M4 and Semaglutide on random blood glucose in diabetic mice.
Figure 4:
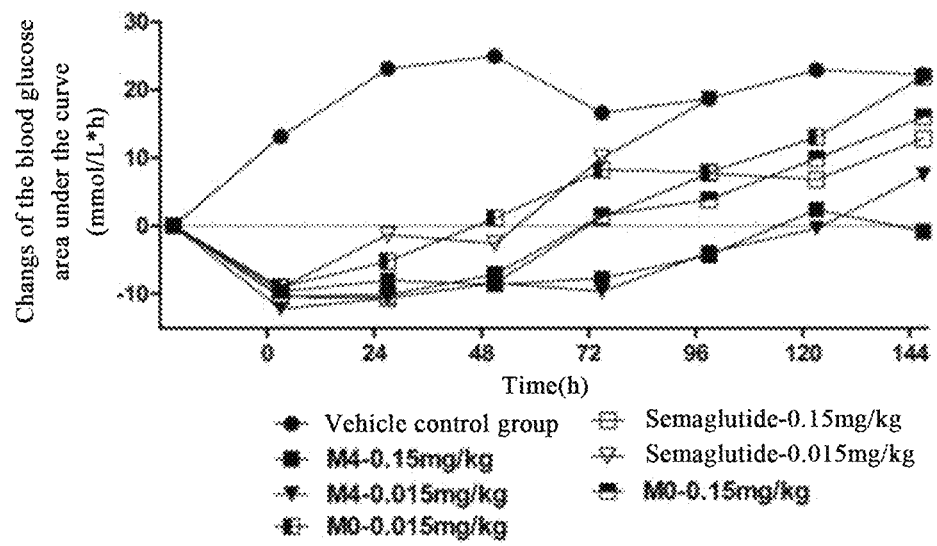
FIG. 4 shows the effects of different doses of M0, M4 and Semaglutide on the blood glucose area under the curve of diabetic mice.

The results are shown in Tables 7, 8 and 9, and FIGS. 2, 3 and 4.

TABLE 7

Fasting blood glucose changes of mice in each test group

| | | Average changes of fasting blood glucose after administration (mM) | | | | | | | |
|---|---|---|---|---|---|---|---|---|---|
| Groups | Administration dosage (mg/kg) | −21 h | 3 h | 27 h | 51 h | 75 h | 99 h | 123 h | 147 h |
| Vehicle control | — | 0.0 | 3.8 | 4.2 | 6.1 | 3.4 | 6.8 | 8.9 | 8.7 |
| M4 | 0.15 | 0.0 | −4.2 | −4.5 | −3.8 | −2.5 | −2.0 | 0.0 | 1.1 |
| | 0.015 | 0.0 | −4.4 | −3.3 | −3.2 | −2.6 | 0.4 | 0.6 | 2.3 |

TABLE 7-continued

Fasting blood glucose changes of mice in each test group

| Groups | Administration dosage (mg/kg) | Average changes of fasting blood glucose after administration (mM) | | | | | | |
|---|---|---|---|---|---|---|---|---|
| | | −21 h | 3 h | 27 h | 51 h | 75 h | 99 h | 123 h | 147 h |
| Semaglutide | 0.15 | 0.0 | −3.6 | −3.3 | −3.0 | 3.0 | 3.6 | 3.0 | 4.7 |
| | 0.015 | 0.0 | −4.2 | −2.0 | 0.0 | 1.0 | 3.9 | / | / |
| M0 | 0.15 | 0.0 | −4.1 | −3.0 | −3.2 | −0.7 | 1.4 | 4.4 | 6.7 |
| | 0.015 | 0.0 | −3.5 | −2.7 | −2.4 | 2.5 | 3.9 | 3.7 | 9.8 |

Note:
"−21 h" represents the fasting blood glucose base before administration.

TABLE 8

Average changes of random blood glucose of mice in each test group

| Groups | Administration dosage (mg/kg) | Average changes of random blood glucose after administration (mM) | | | | | | |
|---|---|---|---|---|---|---|---|---|
| | | −5 h | 6 h | 19 h | 43 h | 67 h | 91 h | 115 h | 139 h |
| Vehicle control | — | 0 | −1.7 | −0.8 | 0.9 | 1.9 | 3.7 | 5.2 | 4.8 |
| M4 | 0.15 | 0 | −17.3 | −17.5 | −17.0 | −16.8 | −13.5 | −1.8 | 2.8 |
| | 0.015 | 0 | −16.6 | −15.4 | −14.1 | −12.9 | −9.2 | −1.3 | 3.0 |
| Semaglutide | 0.15 | 0 | −17.6 | −17.5 | −16.1 | −10.0 | 0.4 | 5.2 | 3.6 |
| | 0.015 | 0 | −17.9 | −17.5 | −14.6 | −11.3 | −0.6 | / | / |
| M0 | 0.15 | 0 | −15.7 | −14.8 | −14.1 | −7.1 | 1.7 | 4.5 | 7.8 |
| | 0.015 | 0 | −15.7 | −13.5 | −10.1 | −3.1 | −0.1 | 4.9 | 5.9 |

Note:
"−5 h" represents the random blood glucose base at 5 h before administration.

TABLE 9

Changes of the blood glucose area under the curve (G-AUC) of mice in each test group

| Groups | Administration dosage (mg/kg) | Average changes of the blood glucose area under the curve after administration (mmol/L · h) | | | | | | |
|---|---|---|---|---|---|---|---|---|
| | | −21 h | 3 h | 27 h | 51 h | 75 h | 99 h | 123 h | 147 h |
| Vehicle control | — | 0 | 13.1 | 23.1 | 24.9 | 16.6 | 18.7 | 22.9 | 22.2 |
| M4 | 0.15 | 0 | −9.6 | −8.0 | −8.6 | −7.7 | −4.3 | 2.4 | −0.8 |
| | 0.015 | 0 | −12.2 | −10.6 | −8.4 | −9.6 | −3.9 | −0.4 | 7.5 |
| Semaglutide | 0.15 | 0 | −10.4 | −10.6 | −8.4 | 1.3 | 7.7 | 6.8 | 12.8 |
| | 0.015 | 0 | −9.1 | −1.3 | −2.6 | 10.0 | 18.6 | / | / |
| M0 | 0.15 | 0 | −10.3 | −10.2 | −7.1 | 1.5 | 3.9 | 9.9 | 16.0 |
| | 0.015 | 0 | −9.0 | −5.2 | 1.1 | 8.2 | 7.9 | 13.0 | 21.9 |

Note:
"−21 h" represents the base of blood glucose area under the curve before administration.

The results in Tables 7-9 and FIGS. 2-4 indicate:

Fasting blood glucose: as for M4, at 123h after administration that of the 0.15 mg/kg dosage group returns to the basal blood glucose base before administration, and at 99h after administration that of the 0.015 mg/kg dosage group returns to the basal blood glucose base before administration; as for Semaglutide, at 51h after administration that of the 0.15 mg/kg dosage group returns to the basal blood glucose base before administration, and at 27h after administration that of the 0.015 mg/kg dosage group returns to the basal blood glucose base before administration; as for M0, at 75h after administration that the 0.15 mg/kg dosage group returns to the basal blood glucose base before administration, and at 51h after administration that of the 0.015 mg/kg dosage group returns to the basal blood glucose base before administration; wherein all the reduction values of fasting blood glucose in the 0.015 mg/kg dosage group of M4 at each time point for measurement are not lower than those in the 0.15 mg/kg dosage group of Semaglutide or M0.

Random blood glucose: as for M4, at 115h after administration that of the 0.15 mg/kg dosage group returns to the random blood glucose base before administration, and at 115h after administration that of the 0.015 mg/kg dosage group returns to the random blood glucose base before administration; as for Semaglutide, at 67h after administration that of the 0.15 mg/kg dosage group returns to the random blood glucose base before administration, and at 67h after administration that of the 0.015 mg/kg dosage group returns to the random blood glucose base before administration; as for M0, at 67h after administration that of the 0.15 mg/kg dosage group returns to the random blood glucose base before administration, and at 67h after administration that of the 0.015 mg/kg dosage group returns to the random blood glucose base before administration; wherein all the inhibitory effects on random blood glucose in the 0.015 mg/kg dosage group of M4 at each time point for measurement are not lower than those in the 0.15 mg/kg dosage group of Semaglutide or M0.

Blood glucose area under the curve (G-AUC): as for M4, at 99h after administration that of the 0.15 mg/kg dosage group returns to the base of blood glucose area under the curve before administration, and at 99h after administration that of the 0.015 mg/kg dosage group returns to the base of blood glucose area under the curve before administration; as for Semaglutide, at 51h after administration that of the 0.15 mg/kg dosage group returns to the base of blood glucose area under the curve before administration, and at 51 h after administration that of the 0.015 mg/kg dosage group returns to the base of blood glucose area under the curve before administration; as for M0, at 51h after administration that of the 0.15 mg/kg dosage group returns to the base of blood glucose area under the curve before administration, and at 27h after administration that of the 0.015 mg/kg dosage group returns to the base of blood glucose area under the curve before administration; wherein all the values of blood glucose area under the curve in the 0.015 mg/kg dosage group of M4 at each time point for measurement are not lower than those in the 0.15 mg/kg dosage group of Semaglutide or M0.

These glucose-lowing results indicate that: after a single subcutaneous injection of M4, or Semaglutide, or M0, each group shows a significant glucose-lowing effect, however, M4 has the best glucose-lowing effect. The glucose-lowing effect of the 0.015 mg/kg dosage of M4 is comparable to that of the 0.15 mg/kg dosage of Semaglutide, or that of the 0.15 mg/kg dosage of M0.

Example 12: Research on the Stability of M4 and Semaglutide Against Enzymatic Degradation Pepsin (3200-4500U/mg protein, from Sigma, catalog number: P6887), trypsin (approximately 10000AEE U/mg protein, from Sigma, catalog number: T8003).

(1) Reaction Solution

A: Reaction buffer of pepsin: three 20 mM citric acid-phosphate buffers with different pH (2.6, 4.0, and 7.4) are prepared, then adding 0.005% Tween 20 and 0.001% BSA to prepare a reaction buffer of pepsin.

B: Reaction buffer of trypsin: three 20 mM citric acid-phosphate buffers with different pH (4.0, 6.8, and 8.0) are prepared, then adding 0.005% Tween 20 and 0.001% BSA to prepare a reaction buffer of trypsin.

C: Simulated gastric fluid containing pepsin (SGF): obtained by taking 5 ml of 0.1M hydrochloric acid and adding and dissolving 0.019 g of pepsin.

D: Simulated intestinal fluid containing trypsin (SIF): obtained by taking 0.0684 g of potassium dihydrogen phosphate, adding 2.5 ml of water to dissolve it, adding 0.77 ml of 0.2M sodium hydroxide solution and 5 ml of water, and then adding and dissolving 0.1001 g of trypsin; the pH is measured as 6.82, then diluting by adding water to 10 ml.

(2) Sample Preparation

M4 and Semaglutide samples are taken and respectively diluted to 1.33 mg/ml with PB buffer at pH 7.4 as the stock solutions of the test samples.

(3) Pepsin Degradation Experiments

An appropriate amount of the stock solution of each test samples is taken respectively, then diluted to 0.06 mg/ml with reaction buffers of pepsin with different pH; reaction solution of each group is divided into 1 ml/tube, a total of 7 tubes, then mixing well and incubating in a 37° C. water bath for 30 min. 1 tube without SGF is taken out as the 0 point of enzyme-free reaction (recorded as −5 min point), and then other 6 tubes are taken out and added with SGF separately and mixed well, one tube of them is immediately added with an appropriate volume of 1M NaOH to quench the reaction, acting as the 0 point after adding enzyme (recorded as 0 min point), and the remaining 5 tubes are placed at 37° C. continuously for reaction; and one group is taken out at 5 min, 10 min, 20 min, 35 min and 50 min respectively and added with an appropriate volume of 1M NaOH respectively to quench the reaction. All tubes in all experimental groups are ensured that the total volume after termination of the reaction is the same.

(4) Trypsin Degradation Experiments

An appropriate amount of the stock solution of the test sample is taken respectively, then diluting it to 0.06 mg/ml with reaction buffers of trypsin with different pH; each group of reaction solution is divided into 1 ml/tube, a total of 7 tubes, then mixing well and incubating in a 37° C. water bath for 30 min. 1 tube without SIF is taken out as the 0 point of enzyme-free reaction (recorded as −5 min point), and then other 6 tubes are taken out to add SIF separately and mix well, among them one tube is immediately added an appropriate volume of 6M HCl to quench the reaction, as the 0 point after adding enzyme (recorded as 0 min point), and the remaining 5 tubes are placed at 37° C. continuously for reaction; and one group is respectively taken out at 5 min, 10 min, 20 min, 35 min and 50 min to add an appropriate volume of 6M HCl respectively to quench the reaction. All tubes in all experimental groups are ensured that the total volume after termination of the reaction is the same.

HPLC assay is performed with samples from the enzyme degradation experiment. The peak area of the main peak of the sample without enzyme reaction at 0 point (recorded as −5 min) is used as the basal peak area, and the remaining percentage of the peak area of the main peak at different time points after enzyme addition is calculated.

Figure 5:
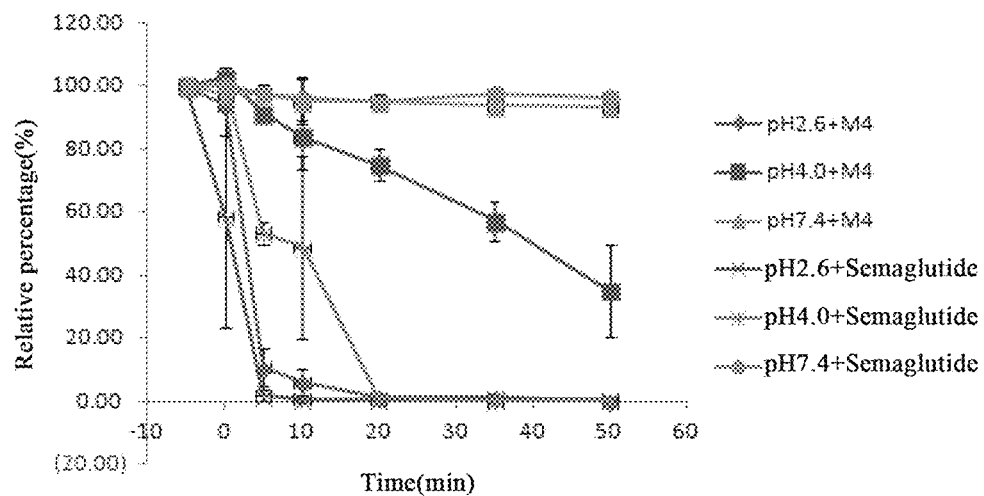
FIG. 5 shows the trend graph of M4 and Semaglutide molecules against pepsin degradation.

Experimental data of pepsin degradation (n=3) shows (FIG. 5) that, the degradation rates of M4 and Semaglutide molecules under acidic condition (pH 2.6) are comparable, which is due to the highest pepsin activity at this pH; at neutral pH 7.4, both molecules are basically not degraded, and at this time the activity of gastric protein is the lowest; while at pH 4.0, the degradation rate of Semaglutide is significantly higher than that of M4, the t1/2 of the former is about 10 min, and the t1/2 of the latter is about 45 min, indicating that the ability of M4 against pepsin degradation is significantly better than that of Semaglutide.

Figure 6:
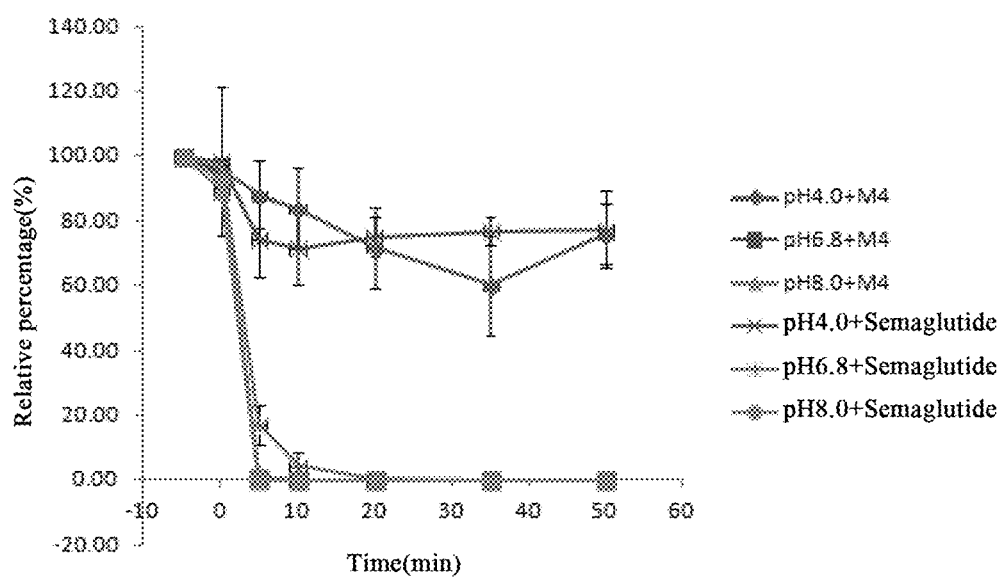
FIG. 6 shows the trend graph of M4 and Semaglutide molecules against trypsin degradation.

Experimental data of trypsin degradation (n=4) shows (FIG. 6) that, the degradation rates of the two are basically the same under the conditions of pH6.8 and 8.0, because trypsin has the highest activity in this pH range; M4 and Semaglutide also show the ability against trypsin degradation under the condition of pH4.0, and there is basically no difference between the two.

The invention claimed is:

1. A derivative of a GLP-1(7-37) analogue or a pharmaceutically acceptable salt thereof, wherein the derivative is: N-$\varepsilon^{23}$-[2-(2-[2-(2-[2-(2-[4-(17-carboxyheptadecanoylamino)-4(s)-carboxybutyrylamino]ethoxy)ethoxy]acetylamino)ethoxy]ethoxy)acetyl](Val$^8$Glu$^{22}$Lys$^{23}$Arg$^{26,34}$ GLP-1(7-37)) peptide (M2), or N-$\varepsilon^{30}$-[2-(2-[2-(2-[2-(2-[4-(17-carboxyheptadecanoylamino)-4(s)-carboxybutyrylamino]ethoxy)ethoxy]acetylamino)ethoxy]ethoxy)acetyl] (Val$^8$Glu$^{22}$Lys$^{30}$Arg$^{26,34}$-GLP-1(7-37)) peptide (M4).

2. A method for preparing the derivative or a pharmaceutically acceptable salt thereof, comprising:
   (1) mixing a solution in which the GLP-1 analogue according to claim 1 is dissolved with a solution in which the extension portion is dissolved;
   (2) adjusting the pH to 4-5 to quench the reaction, standing until a precipitate is generated, and then collecting the precipitate; and
   (3) adding TFA to the precipitate, and adjusting the pH to 7.5-8.5 to quench the reaction.

3. The method according to claim 2, further comprising: adding triethylamine to a solution in which the GLP-1 analogue is dissolved, followed by mixing with a solution in which the extension portion is dissolved.

4. The method according to claim 2, wherein the solution of the extension portion is dissolved by acetonitrile.

5. A pharmaceutical composition comprising the derivative or a pharmaceutically acceptable salt thereof according to claim 1, and a pharmaceutically acceptable excipient.

6. A method for treating diabetes or diabetic complications, comprising: administering a prophylactically or therapeutically effective amount of the derivative or the pharmaceutically acceptable salt thereof according to claim 1 to a subject.

7. The method according to claim 6, wherein the diabetic complication is diabetic nephropathy.

8. A method for reducing blood glucose, increasing glucose tolerance, reducing islet β-cell apoptosis, enhancing islet β-cell function, increasing islet β-cell number, and/or restoring islet β-cell glucose sensitivity, comprising: administering a therapeutically effective amount of the derivative or the pharmaceutically acceptable salt thereof according to claim 6 to a subject.

9. The method according to claim 8, wherein said reducing blood glucose includes reducing fasting blood glucose and/or postprandial blood glucose.

10. A kit comprising: a container in which the pharmaceutical composition according to claim 5 is contained, and a package insert, wherein the package insert contains instructions for use of the pharmaceutical composition.

11. The kit according to claim 10, further comprising a container containing one or more other medicaments.

12. The kit according to claim 11, wherein the one or more other medicaments are other medicaments for treating diabetes or diabetic complications.

13. The derivative of a GLP-1(7-37) analogue or pharmaceutically acceptable salt thereof according to claim 1 wherein the derivative is N-$\varepsilon^{23}$-[2-(2-[2-(2-[2-(2-[4-(17-carboxyheptadecanoylamino)-4(s)-carboxybutyrylamino]ethoxy)ethoxy]acetylamino)ethoxy]ethoxy)acetyl] (Val$^8$Glu$^{22}$Lys$^{23}$Arg$^{26,34}$-GLP-1(7-37)) peptide (M2).

14. The derivative of a GLP-1(7-37) analogue or pharmaceutically acceptable salt thereof according to claim 1 wherein the derivative is N-$\varepsilon^{30}$-[2-(2-[2-(2-[2-(2-[4-(17-carboxyheptadecanoylamino)-4(s)-carboxybutyrylamino]ethoxy)ethoxy]acetylamino)ethoxy]ethoxy)acetyl] (Val$^8$Glu$^{22}$Lys$^{30}$Arg$^{26,34}$-GLP-1(7-37)) peptide (M4).

* * * * *